(12) United States Patent
Naishadham et al.

(10) Patent No.: US 9,759,688 B2
(45) Date of Patent: Sep. 12, 2017

(54) HIGHLY SENSITIVE STANDOFF GAS SENSING USING CARBON NANOTUBES AND INTEGRATED WIRELESS DEVICES

(71) Applicant: Georgia Tech Research Corporation, Atlanta, GA (US)

(72) Inventors: Krishna Naishadham, Smyrna, GA (US); Xiaojuan Song, Duluth, GA (US); Brent Wagner, Marietta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 13/781,857

(22) Filed: Mar. 1, 2013

(65) Prior Publication Data
US 2013/0230429 A1    Sep. 5, 2013

Related U.S. Application Data

(60) Provisional application No. 61/605,362, filed on Mar. 1, 2012.

(51) Int. Cl.
*G01N 29/036* (2006.01)
*G01N 29/02* (2006.01)
(Continued)

(52) U.S. Cl.
CPC ......... *G01N 29/036* (2013.01); *G01N 29/022* (2013.01); *G01N 29/2481* (2013.01);
(Continued)

(58) Field of Classification Search
CPC .............. B82Y 10/00; D10B 2101/122; G02F 2001/1515; H01G 11/36; H01L 51/0048
(Continued)

(56) References Cited

U.S. PATENT DOCUMENTS

2007/0158209 A1*   7/2007   Kang et al. .................. 205/775

OTHER PUBLICATIONS

Zhang, Ting et al. "Poly(m-aminobenzen sulfonic acid) functionalized single-walled carbon nanotubes based gas sensor," Nanotechnology, vol. 18, 2007, p. 1-6.*
(Continued)

*Primary Examiner* — Dennis M White
*Assistant Examiner* — Bryan Kilpatrick
(74) *Attorney, Agent, or Firm* — Troutman Sanders LLP; Ryan A. Schneider; Parker D. Hancock

(57) ABSTRACT

A gas sensor utilizing carbon nanotubes (CNTs) is disclosed. The sensor can include a patch antenna, a feed line, and a stub line. The stub line can include a carbon nanotube (CNT) thin-film layer for gas detection. The CNTs can be functionalized to detect one or more analytes with specificity designed to detect, for example, environmental air contaminants, hazardous gases, or explosives. The sensor can provide extremely sensitive gas detection by monitoring the shift in resonant frequency of the sensor circuit resulting from the adsorption of the analyte by the CNT thin-film layer. The sensor can be manufactured using inkjet printing technologies to reduce costs. The integration of an efficient antenna on the same substrate as the sensor enables wireless applications of the sensor without additional components, for wireless standoff chemical sensing applications including, for example, defense, industrial monitoring, environmental sensing, automobile exhaust analysis, and healthcare applications.

18 Claims, 19 Drawing Sheets

(51) Int. Cl.
  *G01N 29/24* (2006.01)
  *H01G 11/36* (2013.01)
  *H01L 51/00* (2006.01)
(52) U.S. Cl.
  CPC .. *D10B 2101/122* (2013.01); *G01N 2291/021* (2013.01); *H01G 11/36* (2013.01); *H01L 51/0048* (2013.01)
(58) Field of Classification Search
  USPC ............ 977/742, 853; 422/83; 427/127, 600
  See application file for complete search history.

(56) References Cited

OTHER PUBLICATIONS

Yang, Li et al. "A Novel Conformal RFID-enabled Module Utilizing Inkjet-printed Antennas and Carbon Nanotubes for Gas-detection Applications," IEEE Antennas and Wireless Propagation Letters, vol. 8, 2009, p. 653-656.*

* cited by examiner

HIGHLY SENSITIVE STANDOFF GAS SENSING USING CARBON NANOTUBES AND INTEGRATED WIRELESS DEVICES

CROSS REFERENCE TO RELATED APPLICATIONS

This Application claims priority to, and benefit under 35 USC §119(e) of, U.S. Provisional Patent Application Ser. No. 61/605,362, entitled "Highly Sensitive Standoff Gas Sensing using Carbon Nanotubes," filed Mar. 1, 2012, which is hereby incorporated by reference as if fully set forth below.

BACKGROUND OF THE INVENTION

1. Field of the Invention

Embodiments of the present invention relate generally to gas sensors, and more specifically to highly sensitive gas sensors utilizing carbon nanotubes and integrated antennas for wireless applications.

2. Background of Related Art

Carbon nanotubes (CNTs) are long thin cylinders of carbon with a typical diameter ranging from approximately 1 nm to 100 nm. Carbon nanotubes have a number of advantageous properties including, for example, their size, shape, and physical properties. Due to their large tubular surface area, with a hollow inner core and a thin cylindrical wall, CNTs exhibit moderate to high surface adsorption. This adsorption, in turn, can produce appreciable changes in electrical conductivity of the CNTs at room temperature in the presence of various substances.

Conventional CNT-based gas sensors, which generally rely on detecting either a change in the resonant frequency or change in the amplitude upon exposure to the analyte of interest, provide insufficient sensitivity for many applications. Previous designs have included, for example, a 3.9 GHz patch resonator coated entirely with a mixture of single-walled nanotubes (SWNT) in powder form for ammonia detection.[1] When the CNT coating is exposed to ammonia, it changes the effective permittivity and shifts the resonant frequency of the resonator. Unfortunately, minimal frequency shifts have been detected (approximately 5-MHz), even in the presence of high ammonia concentration (e.g., up to 1000 ppm). Similar sensors have also reported a shift of approximately 7 MHz when the resonator was completely immersed in methanol.[2]

[1] S. Chopra, A. Pham, J. Gaillard, A. Parker, and A. M. Rao, "Carbon-nanotube-based resonant-circuit sensor for ammonia," *Appl. Phys. Lett.*, vol. 80, no. 24, pp. 4632-4634, June 2002.
[2] Y. Zhou, Y. Bayram, F. Du, L. Dai, and J. L. Volakis, "Polymer-carbon nanotube sheets for conformal load bearing antennas," *IEEE Trans. Antennas Propag.*, vol. 58, no. 7, pp. 2169-2175, July 2010.

While these shifts are detectable in a laboratory setting, in a remote sensing mode, such small detection shifts can lead to false alarms. Indeed, variances in the resonator fabrication due to manufacturing tolerances may cause changes of the same magnitude. Furthermore, the large losses in the resonator, caused by CNT loading, limit sensor sensitivity and preclude effective integration of wireless transmission devices such as antennas. As a result, these configurations are not suitable for low-cost and/or wireless applications for standoff sensing, for example.

Other sensors have been manufactured comprising a composite of multi-walled nanotubes (MWNTs) and $SiO_2$ (which simply acts to bind the MWNTs) placed over a planar LC-resonator printed on silicon. This configuration can be fabricated by photolithography on a printed circuit board substrate.[3] The sensor detects the change in the effective dielectric constant of the circuit caused by surface interaction with the gas. Again, due to very small variation in the dielectric constant upon exposure to gas, however, this sensor also suffers from low sensitivity, thus limiting its practical uses.

[3] K. G. Ong, K. Zheng, and C. A. Grimes, "A wireless passive carbon nanotube-based gas sensor," IEEE Sensors J., vol. 2, no. 2, pp. 82-88, April 2002.

Still other types of CNT-based gas sensors rely on the change in amplitude of the reflected signal (i.e., the return loss) or the transmitted signal for detection. Unfortunately, this method is susceptible to interference and noise, which can also lead to false readings. Conversely, relying on the shift of the resonant frequency—assuming the shift in frequency is sufficiently large to enable accurate detection—is effective for remote sensing because the frequency shift is relatively insensitive to detrimental influences such as noise and interference.

What is needed, therefore, is a gas sensor utilizing the advantageous properties of CNTs. The sensor should take advantage of the relatively stable shift in resonant frequency, yet improve the sensitivity thereof. The sensor should use conventional manufacturing techniques to provide improved, low-cost gas detectors. The sensor should incorporate a low-cost, high sensitivity antenna to enable accurate detection and wireless transmission over standoff distances of several meters to several kilometers. It is to such a system that embodiments of the present invention are primarily directed.

BRIEF SUMMARY OF THE INVENTION

Embodiments of the present invention relate generally to gas sensors, and more specifically to highly sensitive gas sensors utilizing carbon nanotubes integrated with antennas and electronics that enable wireless remote sensing. In some embodiments, the sensor can comprise a patch antenna, plurality of radiating elements, or other antenna configuration in electrical communication with a carbon nanotube (CNT) sensor element. The sensor can enable gas detection by detecting the shift in resonant frequency of the circuit in the presence of an analyte.

In some embodiments, the CNTs can be modified to provide sensitivity to a particular analyte. In some embodiments, the sensor can be configured to detect ammonia. In this configuration, the CNTs can be single walled nanotubes (SWNTs) that have been modified using covalent bonding with poly(m-aminobenzene sulfonic acid) (PABS). In this configuration, the change in impedance of the CNT sensor as the result of adsorption of ammonia molecules can result in an easily measurable shift in resonant frequency of the circuit. In addition to providing a measurable shift in resonant frequency, the integrated antenna system can enable duplex communication to/from the sensor circuit to enable low-cost wireless sensing.

Embodiments of the present invention can comprise a gas sensor comprising an antenna with a first end, a feed line, with a first end and a second end, the second end in electrical communication with the first end of the antenna, a carbon nanotube (CNT) thin-film layer, with a first end and a second end, the first end in electrical communication with the feed line, and a stub line, with a first end and a second end, the first end in electrical communication with the second end of the CNT thin-film layer. In some embodiments, the antenna, feed line, and stub line can be integrated with the CNT thin-film layer on a first substrate. In some embodiments, the first substrate can comprise paper.

In some embodiments, the CNT thin-film layer can comprise single walled carbon nanotubes (SWNTs). In some embodiments, the SWNTs can be functionalized with a first chemical compound to provide a chemical interaction with a first analyte. The use of poly(m-aminobenzene sulfonic acid) (PABS) functionalizes the SWNTs for the detection of ammonia ($NH_3$), for example.

Embodiments of the present invention can also comprise a gas sensor comprising an antenna with a first end and a second end, a feed line, with a first end and a second end, the second end in electrical communication with the first end of the antenna, a carbon nanotube (CNT) thin-film layer, with a first end and a second end, the first end in electrical communication with the second end of the antenna, and a stub line, with a first end and a second end, the first end in electrical communication with the second end of the CNT thin-film layer. In some embodiments, the antenna, feed line, and stub line can comprise conductive ink printed on a first substrate and can be integrated with the CNT film layer on the first substrate.

In some embodiments, the first substrate comprises a liquid crystal polymer. In some embodiments, the CNT thin-film layer can comprise single walled carbon nanotubes (SWNTs). The SWNTs can be functionalized with a first chemical compound, such as poly(m-aminobenzene sulfonic acid) (PABS), for example, to provide a chemical interaction with a first analyte (e.g., $NH_3$).

Embodiments of the present invention can also comprise a method of manufacturing a sensor comprising providing a first substrate, printing an antenna, with a first end and a second end, on the first substrate, printing a feed line, with a first end and a second end, the second end in electrical communication with the first end of the antenna, printing a carbon nanotube (CNT) thin-film layer, with a first end and a second end, the first end in electrical communication with the feed line, and printing a stub line, with a first end and a second end, the first end in electrical communication with the second end of the CNT thin-film layer. In some embodiments, one or more of the printing steps can be performed using an inkjet printer. In some embodiments, the antenna, feed line, and stub line can be printed using conductive ink and can be integrated with the CNT film layer on the first substrate.

Embodiments of the present invention can further comprise ultrasonicating a plurality of functionalized single walled nanotubes (SWNTs) in water to form a CNT ink for printing the CNT thin-film layer. In some embodiments, the antenna can be a patch antenna.

Embodiments of the present invention can further comprise method of manufacturing a sensor comprising providing a first substrate, printing an antenna, with a first end and a second end, on the first substrate, printing a feed line, with a first end and a second end, the second end in electrical communication with the first end of the antenna, printing a carbon nanotube (CNT) thin-film layer, with a first end and a second end, the first end in electrical communication with the second end of the antenna, and printing a stub line, with a first end and a second end, the first end in electrical communication with the second end of the CNT thin-film layer. In some embodiments, one or more of the printing steps can be performed using silk screening. In some embodiments, the antenna, feed line, and stub line can be printed using conductive ink and can be integrated with the CNT film layer on the first substrate.

In some embodiments, the method can also comprise ultrasonicating a plurality of functionalized single walled nanotubes (SWNTs) in water to form an ink for printing the CNT thin-film layer. In some embodiments, the first substrate can comprise photo paper.

These and other objects, features and advantages of the present invention will become more apparent upon reading the following specification in conjunction with the accompanying drawing figures.

DETAILED DESCRIPTION OF THE INVENTION

Figure 1:
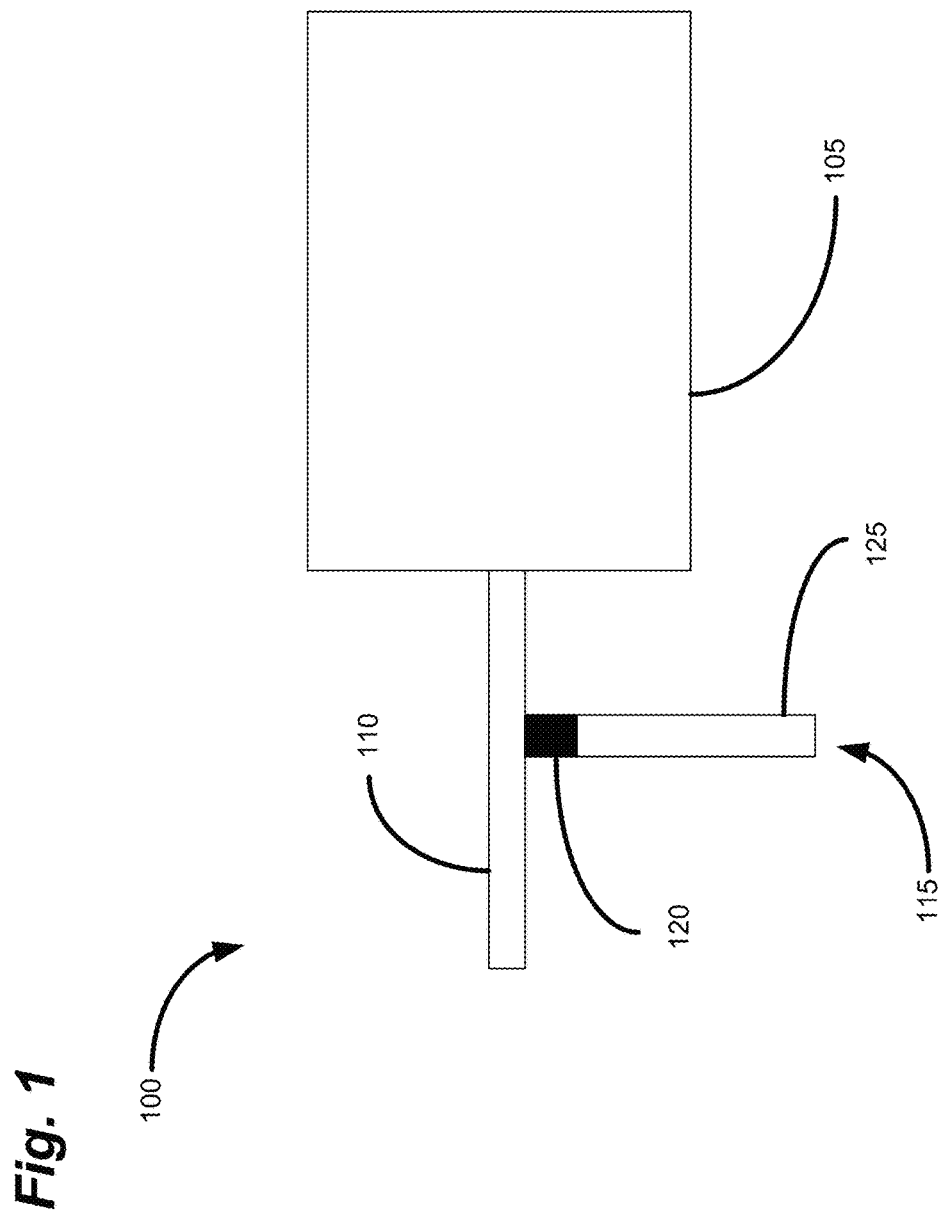
FIG. 1 depicts a CNT film gas sensor printed circuit, in accordance with some embodiments of the present invention.

Embodiments of the present invention relate generally to gas sensors, and more specifically to highly sensitive gas sensors utilizing carbon nanotubes. In some embodiments, the sensor can comprise one or more electrodes printed on a suitable substrate. The electrodes can be in electrical communication (e.g., integrated) with a thin-film sensor comprising carbon nanotubes (CNTs) deposited outside the radiating aperture of a printed antenna, such as a patch antenna, for example, to form a wireless sensor node. The CNTs can be electrically and/or chemically modified using one of several techniques to provide sensitivity and selectivity to various chemical compounds. The presence and quantity of these compounds can be detected by the shift in resonant frequency of the resulting circuit.

To simplify and clarify explanation, the system is described below as a sensor for detecting ammonia levels. One skilled in the art will recognize, however, that the invention is not so limited. The system can also be deployed to detect other gases, for example, by modification of the CNT sensing film (e.g., through polymer functionalization). In addition, the system is described below as using silver ink printed on various types of paper; however, other substrates and conductive materials could be used. The system can be deployed to detect gas levels related to, for example and not limitation, hazardous gases (for example sarin and other nerve gases), exhaust gas analysis, and atmospheric monitoring.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. Any dimensions listed in the various drawings are for illustrative purposes only and are not intended to be limiting. Other dimensions and proportions are contemplated and intended to be included within the scope of the invention.

As discussed above, a problem with current gas sensors utilizing CNTs is that they do not provide sufficient sensitivity, even in response to high concentration levels of analyte. Conventionally, changes in resonant frequency, for example, have been on the order of 5-7 MHz. Unfortunately, changes this small do not differentiate themselves from changes due to, for example and not limitation, manufacturing tolerances. What is needed, therefore, is a cost-effective sensor that utilizes CNTs, yet provides sufficient sensitivity for accurate gas detection, even at very low concentrations.

To this end, embodiments of the present invention can comprise one or more electrodes, connected with a thin-film CNT sensor surface, and an integrated antenna, such as a patch antenna or other type of printed antenna. In some embodiments, the antenna and the CNT film can be inkjet-printed onto photo-paper, liquid crystal polymer, or similar hydrophobic surface.

Figure 2:
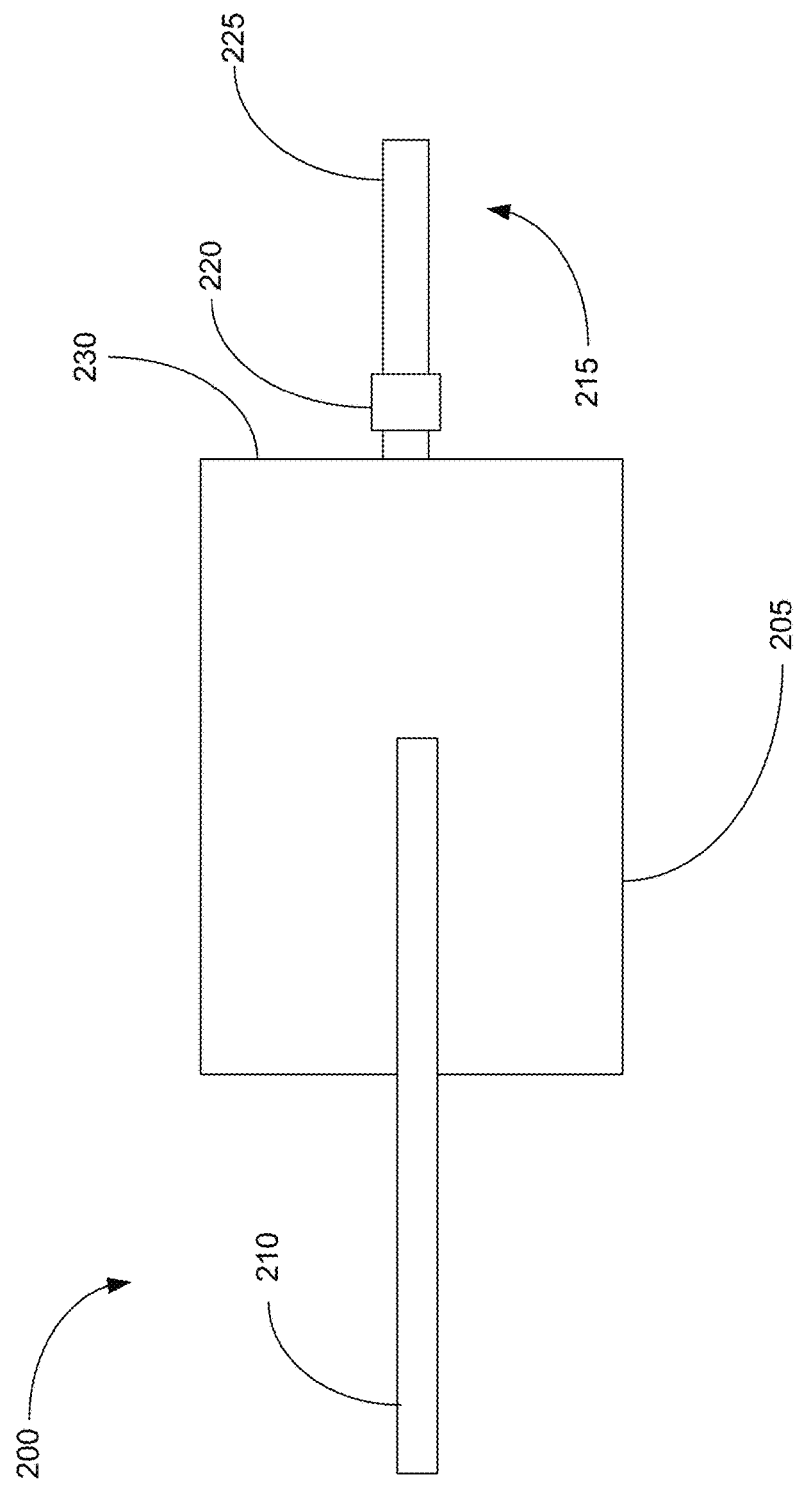
FIG. 2 depicts another CNT film gas sensor printed circuit, in accordance with some embodiments of the present invention.

As shown in FIG. 1, embodiments of the present invention can comprise a gas sensor labeled as printed circuit 100. In some embodiments, the printed circuit 100 can comprise a patch antenna 105, a feed line 110, and a stub 115. The stub 115 can comprise, for example, an electrode 125 connected to the circuit 100 covered with a CNT thin-film layer 120. Similarly, as shown in FIG. 2, in some embodiments, the circuit 200 can also comprise a patch antenna 205 with a feed 210 and stub 215. As before, the stub 215 can comprise an electrode 225 connected to the circuit 200 with a CNT film layer 220. In either configuration, when exposed to the appropriate analyte, the capacitance of the CNT layer 220 (and thus, the stub 110) increases, shifting the resonant frequency of the circuit 100, 200. As discussed below, this type of RF detection provides very sensitive gas detection.

SWNT Chemical Functionalization

Chemical functionalization is a method to enhance both the processability and the sensing performance of singled walled nanotubes (SWNTs). It enables the unique properties of SWNTs to be coupled to other materials, such as conducting polymers, metals, and metal oxides, to create hybrid sensing materials with enhanced sensitivity, selectivity, and faster response time. In addition, the contamination can improve the dissolution and dispersion of SWNTs in various solvents, including water, which enables cost-effective application methods, such as spin coating, dip coating, screen printing, simple dispensing, or ink jet printing, for example, to be used to fabricate sensors. Chemical surface modification of nanotubes by attaching functional groups can also enable stable suspensions and solutions. This process generally alters the original electrical properties of the nanotubes, however, which should be accounted for in the design for new devices. Chemical functionalization with a polymer, for example, can increase the surface resistance of the nanotubes. Covalent sidewall functionalization is one method for modifying the electrical properties of SWNTs for use in many applications. Sidewall functionalization disrupts the $\pi$-bonding system of the carbon and breaks the translational symmetry of SWNTs by introducing saturated sp3 carbon atoms. As a result, electronic and transport properties of SWNTs can be significantly altered. Introducing different chemical groups to the nanotube wall, for example, makes it possible to change the interaction between the nanotubes and the analyte of interest. This reactivity can be used to enhance the sensitivity and selectivity of CNT-based gas sensor devices in applications such as, for example, hazardous gas detection and environmental air-quality monitoring.

Advantageously, covalent bond formation provides a well-controlled route for the introduction of chemical receptors into SWNTs that can enable the isolation and characterization of specific compounds with known electrical conductivity, for example. Covalently functionalized SWNTs can enable the dynamic characterization of the nanotube electronic structure and electrical conductivity in the presence of specific analyte molecules, among other things.

To provide improved sensitivity to ammonia, for example, a poly(m-aminobenzene sulfonic acid) (PABS) functionalized single walled nanotube (SWNT) compound can be used for the gas detection surface 120, 220 of the sensor 100, 200. PABS-SWNT is a water-soluble nanotube-polymer compound, which can be formed by covalently bonding the polymer (PABS) to SWNTs using amide functionalization. The resulting PABS-SWNTs are approximately 1.1 nm in diameter and 0.5-1 µm in length.

Figure 3:
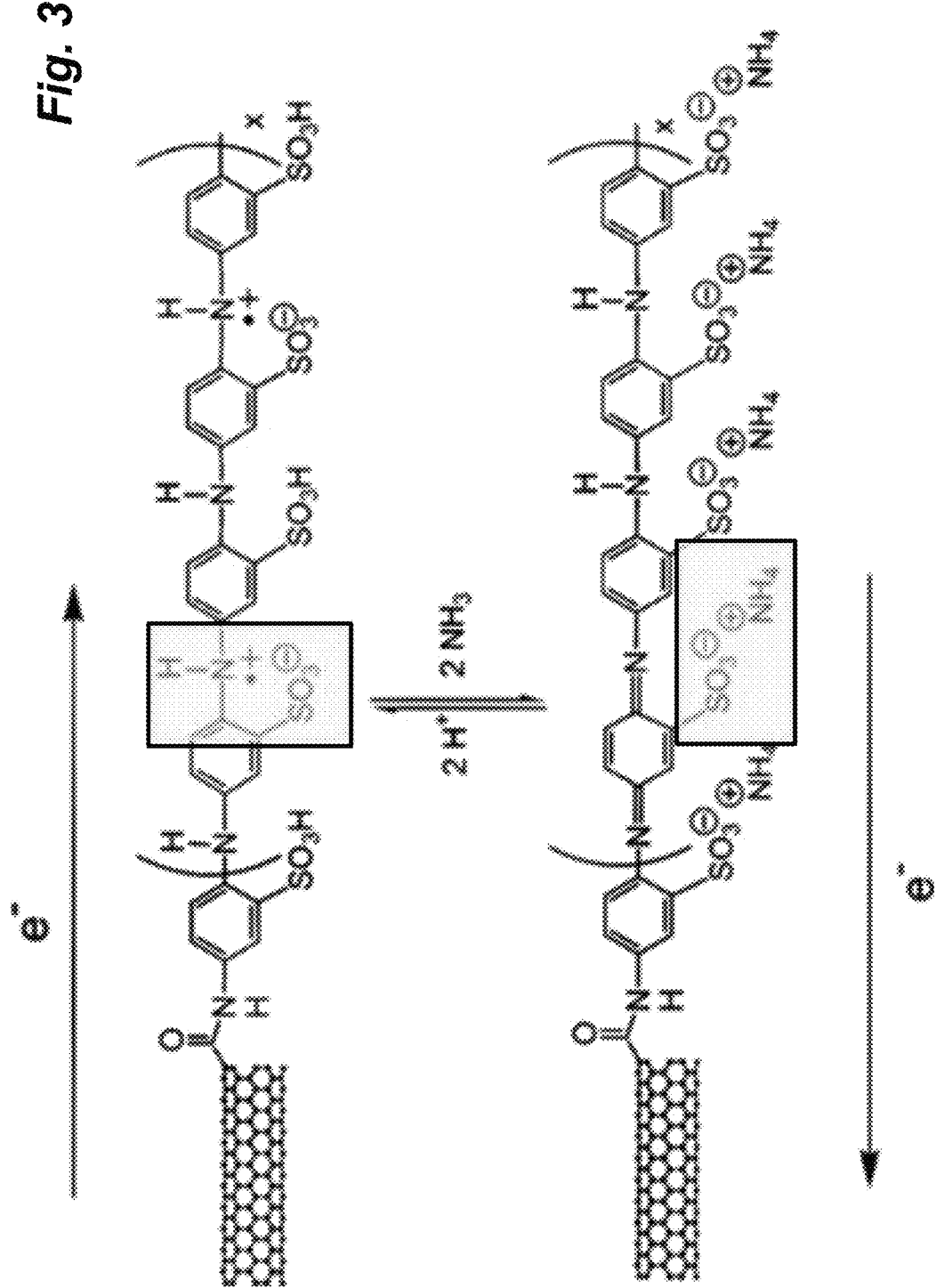
FIG. 3 depicts the mechanism by which carbon nanotubes (CNTs) interact with ammonia, in accordance with some embodiments of the present invention.

The molecular structure and the interaction mechanism of PABS-SWNT with $NH_3$, proposed by Bekyarova et al., are shown in FIG. 3.[4] The PABS functional group that is attached to the SWNT is chemically sensitive to $NH_3$. $NH_3$ sensing occurs by removing a proton ($H^+$) from the side-chain oligomers (the PABS functional group), as shown in the box in FIG. 3. This, in turn, induces electron transfer between the side chain and the SWNTs. In effect, conductivity of the PABS-SWNT molecule is decreased (or the surface resistance increased) because the addition of electrons to the semiconducting SWNTs refills the valence band. As discussed below, the PABS-SWNT sensing film is very effective for $NH_3$ sensing.

[4] E. Bekyarova, l. Kalinina, M. E. Itkis, L. Beer, N. Carbrera, and R. C. Haddon, "Mechanism of ammonia detection by chemically functionalized single-walled carbon nanotubes: in situ electrical and optical study of gas analyte detection," J. Amer. Chem. Soc., vol. 129, pp. 10700-10706, 2007.

Example 1

In some embodiments, a PABS-SWNT solution in water can be prepared for printing CNTs on the substrate. In solid form, however, SWNTs are highly entangled and associated in macroscopic bundles. To disperse these bundles in water, therefore, requires significant effort to break the bundles and dissolve the material. To this end, a portion of material can be sonicated in water.

In some embodiments, PABS-SWNT powder, of the type sold by Carbon Solutions Inc., Riverside, Calif., for example, can be used to prepare a gas sensing film 120, 220 that is reactive in the presence of ammonia ($NH_3$).[5] Aqueous dispersions of PABS-SWNT with a concentration of approximately 5 mg/mL in water can be prepared, for example, by ultrasonication, or other suitable method, followed by deposition onto a paper substrate using, for example and not limitation, ink jet printing, spin coating, or screen printing. Controlled multiple layers of PABS-SWNT can be applied in each fabrication to assure the reproducibility of the gas sensor by achieving a specific DC resistance, among other things.

[5] See, www.carbonsolution.com

To create a solution suitable for inkjet printing on paper, for example, 50 mg of PABS-SWNT was sonicated in 2 ml water for 30 min. Then, 8 ml of additional water was added to this solution and sonicated for an additional 90 min. The dispersion was then allowed to rest overnight at room temperature to observe stability in suspension. After depositing the stable PABS-SWNT dispersion on the antenna stub surface 115, 215, the antenna sensor 100, 200 was then cured for 8 hours at 120 degrees Celsius.

Sensor Design

Given the impedance model of the SWNT film, the sensor 100, 200 can be designed to obtain high RF conductivity through a high-Q/narrow bandwidth design comprising some form of CNT loading of a printed antenna 105, 205. In some embodiments, the CNTs 120, 220 can be deposited in a gap created in a stub 125, 225 connected to a moderate gain patch antenna 105, 205. A significant feature of this design, which enables wireless communication of the detected information, is that the sensing and radiation functions are isolated, as discussed below. Sensitivity from the RF design context utilizes narrowband sampling of the detection phenomena as opposed to the chemical sensitivity of the CNT film 120, 220 itself. As a result, in contrast to previous designs, where resonators were utilized without incorporating remote sensing, embodiments of the present invention can integrate both high sensitivity and remote sensing capabilities (e.g., wireless) within the same structure.

For improved detection sensitivity, a patch antenna topology can be chosen because it has moderately high Q, and thus narrow bandwidth, radiation characteristics. With a narrow bandwidth signal, it is easier to sample and detect the shift in frequency caused by the interaction between ammonia and the CNTs deposited on the patch antenna.

Conventionally, patch resonators have been designed to sense ammonia by covering the entire patch surface with CNTs. Unfortunately, an SWNT generally only retains high conductivity in single tubular form, with conductivity decreasing significantly when mass-deposited in a random configuration (E.G. as a thin-film). An important factor to attain high RF detection sensitivity and simultaneously maintain moderate antenna gain (required for remote communication), therefore, is to minimize the losses in the antenna structure.

As a result, as shown in FIG. 1, in some embodiments, silver ink can be used for the patch antenna 105, with only a small area needed for the CNT film 120 at the tip of the stub 115. Thus, silver covers a large part of the antenna surface 105 (namely, the patch), ensuring moderate efficiency and good radiation pattern, while the high Q of the sensor element 100 results from minimum losses because the CNT film 120 is relatively small. As a result, when the impedance of the CNT thin-film 120 changes due to a chemical reaction with ammonia, the matching conditions at the loading stub 115 will also change. This, in turn, alters the input reflection coefficient at the feed 110.

Figure 4:
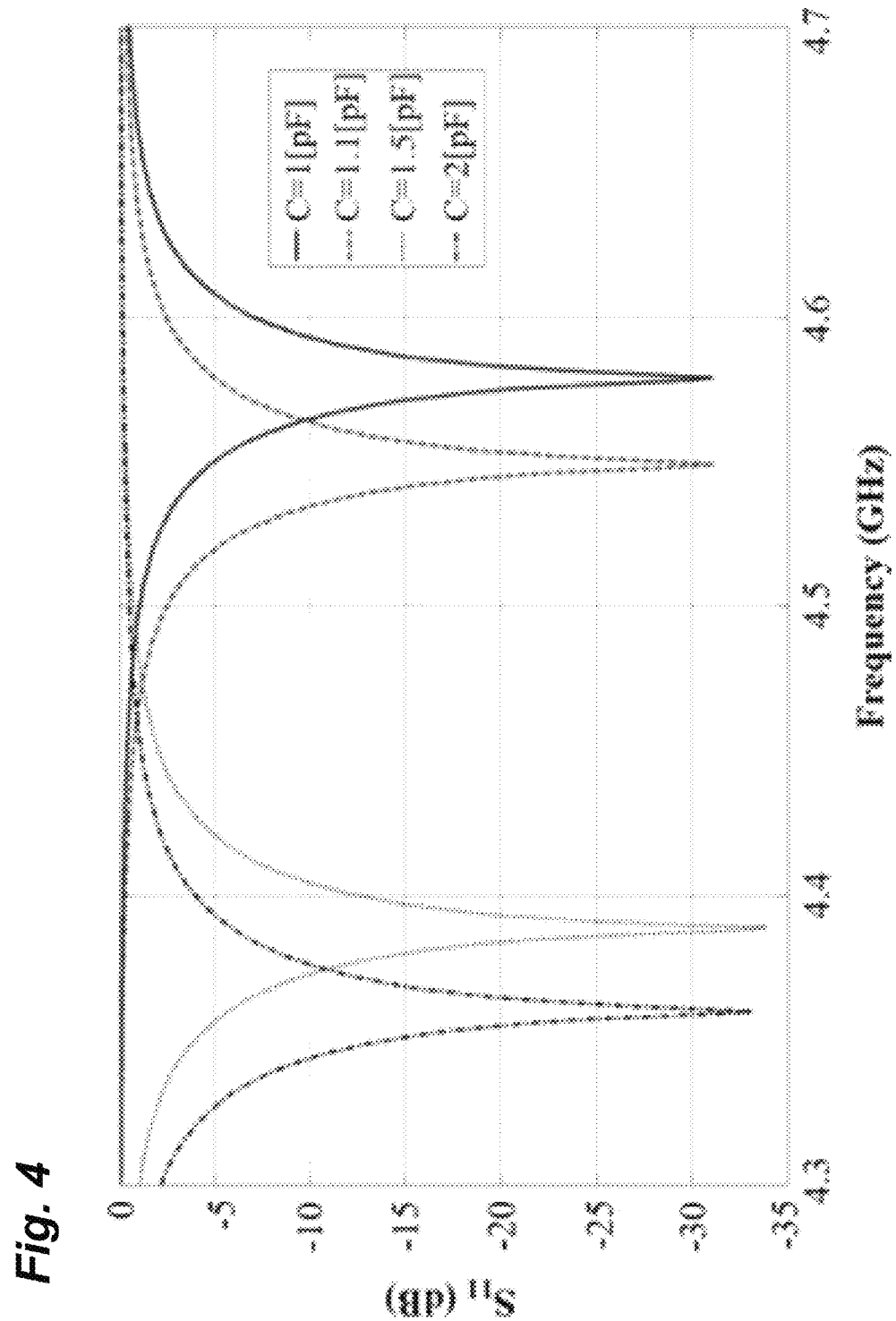
FIG. 4 is a graph depicting numerical predictions of the shift in response due to changes in equivalent capacitance of the CNT layers, in accordance with some embodiments of the present invention.
Figure 5:
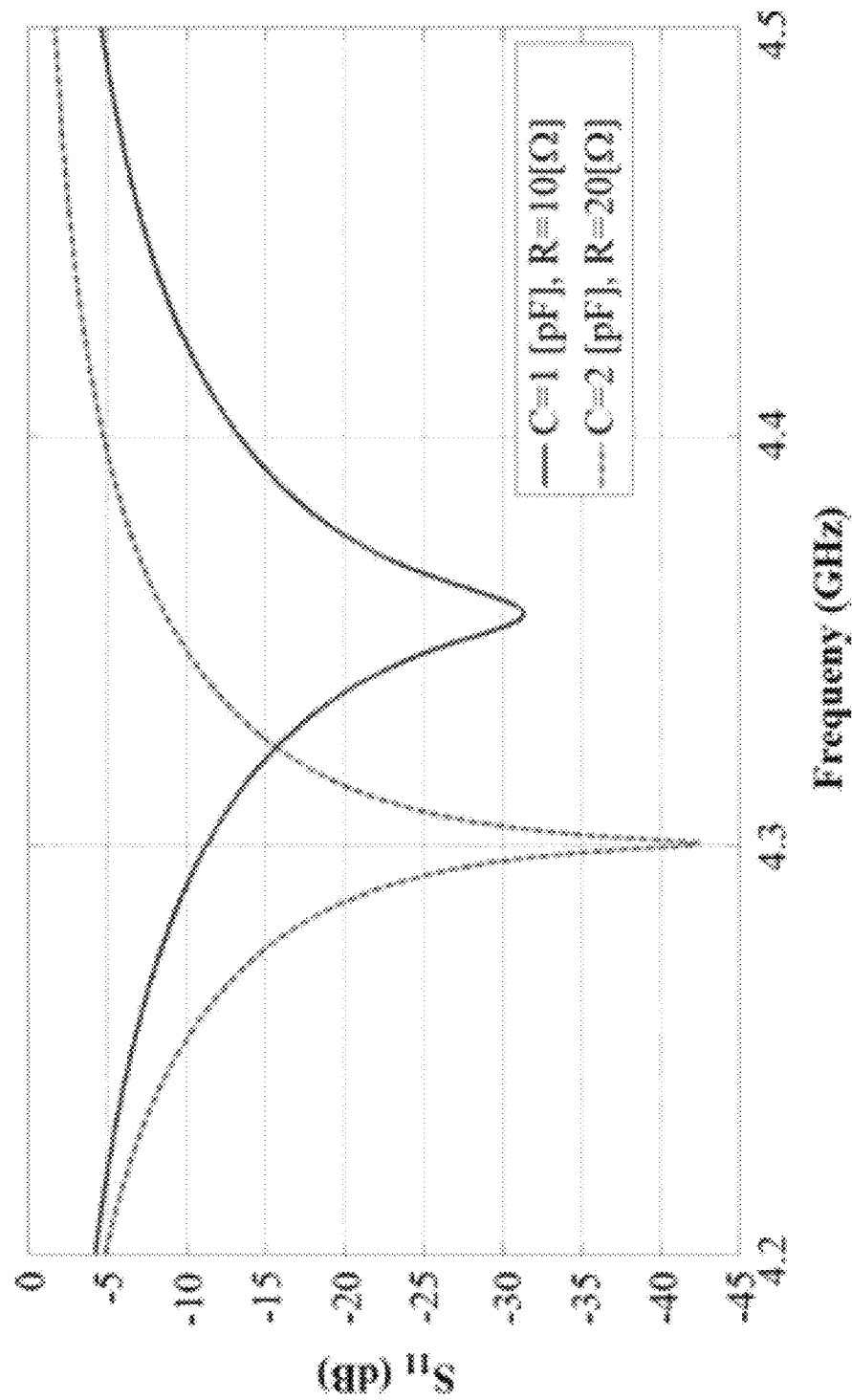
FIG. 5 is a graph depicting numerical predictions of the shift in response due to changes in the equivalent admittance of the CNT layers, in accordance with some embodiments of the present invention.

Consider the design case where the sensor 100 has an equivalent capacitance (C) of the CNT thin-film 120 before gas exposure of 1 pF in parallel with a resistance (R) at a fixed 1Ω, for example. Using this lumped element equivalent circuit representation of the CNT film to load a parallel stub 115, as shown in FIG. 1, a patch antenna 105 can be designed using suitable electromagnetic CAD software (e.g., CST Microwave Studio and Ansoft HFSS) to resonate at approximately 4.5 GHz. Based on FIGS. 4 and 5, the equivalent circuit of the CNT thin-film 125 influences a change in response by shifting the resonant frequency of the sensor upon exposure to ammonia gas. Thus, multiple cases can be numerically investigated. As mentioned, R can be fixed at 1Ω, for example, and C can be varied from 1 to 1.1, 1.5, and 2 pF. The resulting reflection coefficient at the antenna feed terminal 110 is shown in FIG. 4. As shown, a significant frequency shift is observed, even for a relatively minor 10% change in the nominal capacitance.

For further investigation, the equivalent-circuit model can be chosen as a parallel combination of R=10Ω and C=1 pF. Assuming an exposure level that drastically changes R to 20Ω and C to 2 pF, we get the resonant frequency shift of about 60 MHz shown in FIG. 5. Of course, the antenna efficiency in this nominal (i.e., worst case scenario) will be degraded because of the higher CNT losses caused by the higher R. A theoretical calculation shows that the typical antenna efficiency of such a design is approximately 30%. In practice, the CNT thin-film resistance is closer to 1 or 2Ω. As a result, antenna efficiency will be much higher.

Figure 6:
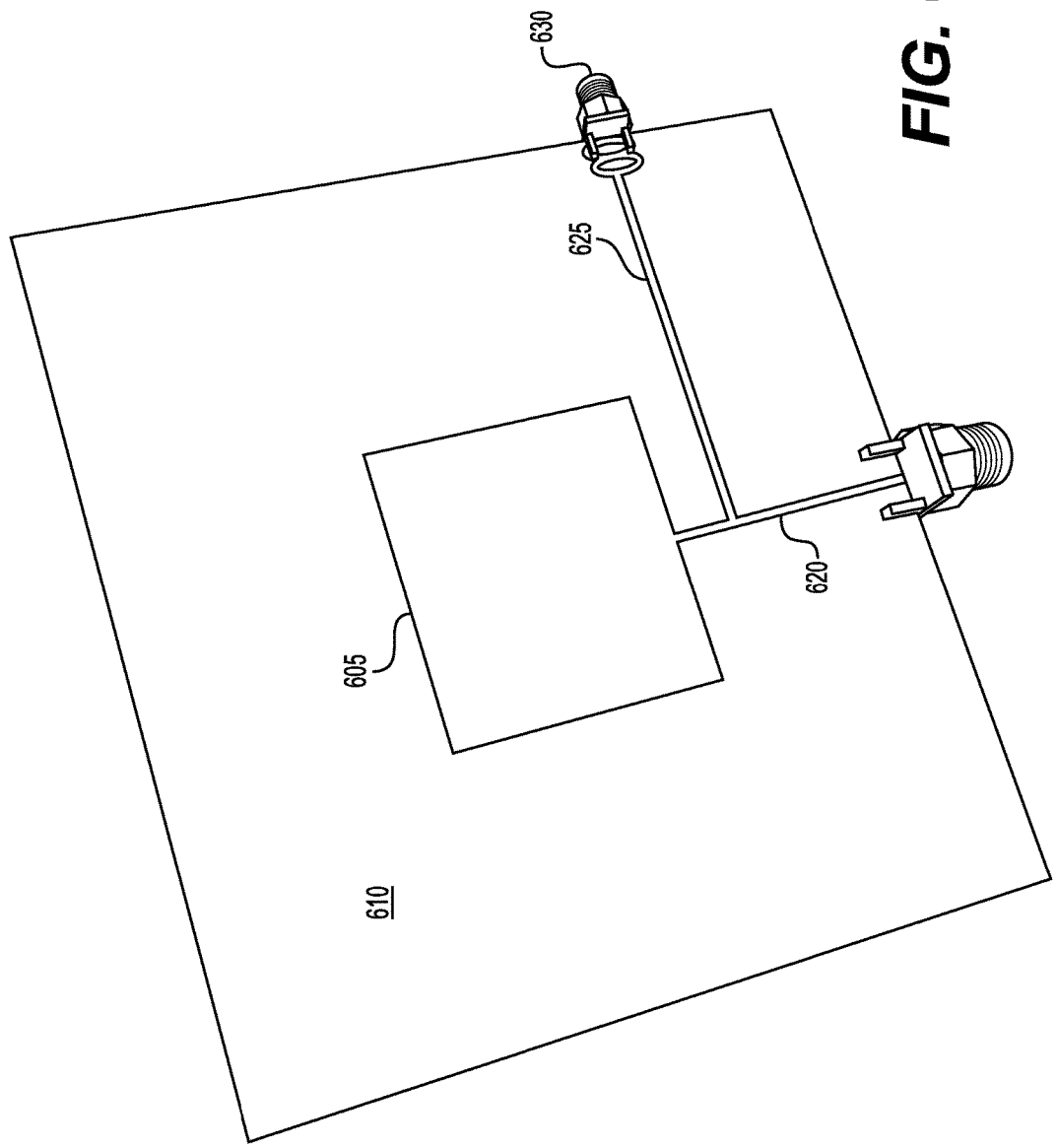
FIG. 6 is a schematic drawing of the gas sensor, in accordance with some embodiments of the present invention.

Based on the above, a loaded patch antenna 605 can be designed and printed on 10-mil-thick paper substrate 610, as shown in FIG. 6. The ground plane on the other side of the substrate (not shown) can be made of a thin copper sheet in electrical communication with the substrate (e.g., glued by conductive epoxy to the paper), though other conductive materials could be used. Similarly, conductive epoxy can be used to solder the connectors 615 onto the silver traces 620, 625 printed on the paper substrate 610, though other connection means (e.g., solder, integrated traces, etc.) could be used. The ground pins of an edge-mount connector 630 can then be connected with the stub end 625 to create the RF short circuit.

The configuration is shown schematically in FIG. 2 which depicts the top view of the patch antenna model 200 comprising a stub 225 placed on the radiating edge 230 to control the resonant frequency. In some embodiments, a small gap can be placed in the stub for CNT film 220 deposition. Deposition can be achieved using, for example and not limitation, ink-jet printing or spray coating. In this case, the antenna 205 was designed for 6 GHz operation and printed on photographic paper about 16 mils (0.4 mm) thick using a Dimatix inkjet printer. Inkjet-printing is a direct-write technology by which the design pattern is transferred directly to the substrate. This has the advantage of obviating the masks used in photoetching techniques, for example. This, combined with the fact that the chemicals used for etching are eliminated, makes this approach both environmentally friendly and cost effective.

The CNT film 220 is essentially a lossy surface coating and thus, affects the efficiency of the antenna 205. The chemical reaction with ammonia, or other analyte of interest to which the CNT film 220 is functionalized, changes the effective permittivity, thereby shifting the resonant frequency. As mentioned above, however, completely coating the resonator 200 with the CNTs 220 increases these losses significantly, limiting the radiation efficiency of the antenna 205 and substantially precluding wireless operation. CNTs are generally only highly conductive in the form of a single tube or a bunch of tubes with aligned domains. As a result, these losses can be minimized by aligning single-walled CNTs in the direction of the electric current on the resonator surface, but this is a cumbersome and expensive operation.

The use of low-cost ink-jet printing, on the other hand, deposits CNTs on the paper substrate producing a mesh of randomly oriented CNTs. With a mesh of randomly oriented CNTs, the conductivity is reduced considerably. To minimize the loss resulting from such a matrix, the antenna and sensor locations can be separated as shown in FIGS. 1 and 2. In this configuration, a small gap proximate the antenna tuning stub 125, 225, isolated from the radiator 105, 205, can be coated with CNTs 120, 220, while the remainder of the circuit 100, 200, including the patch radiator 105, 205, can be fabricated using deposition of highly conductive material (e.g., silver nanoparticles). As a result, the entire radiator can be made of silver, or other conductive materials, and only a very small portion of the sensor 120, 220 comprises CNTs 120, 220. In this configuration, the efficiency of the antenna 105, 205 remains high, and the frequency shift of the return loss is also maximized by the change in impedance of the CNTs 120, 220 upon interaction with ammonia.

Figure 7A:
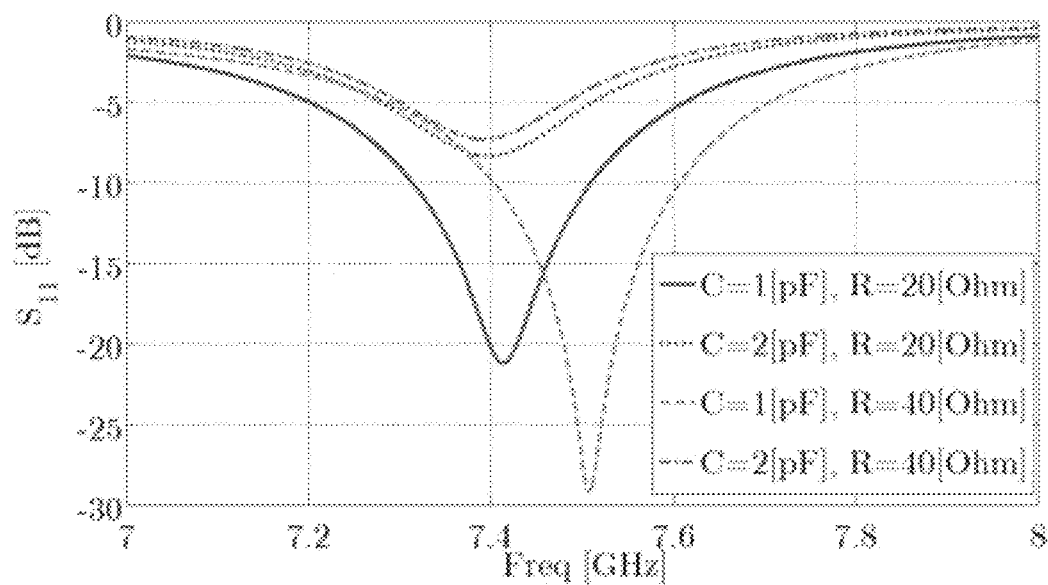
FIG. 7a is a graph depicting the return loss corresponding to change in impedance of the CNT sensor, in accordance with some embodiments of the present invention.
Figure 7B:
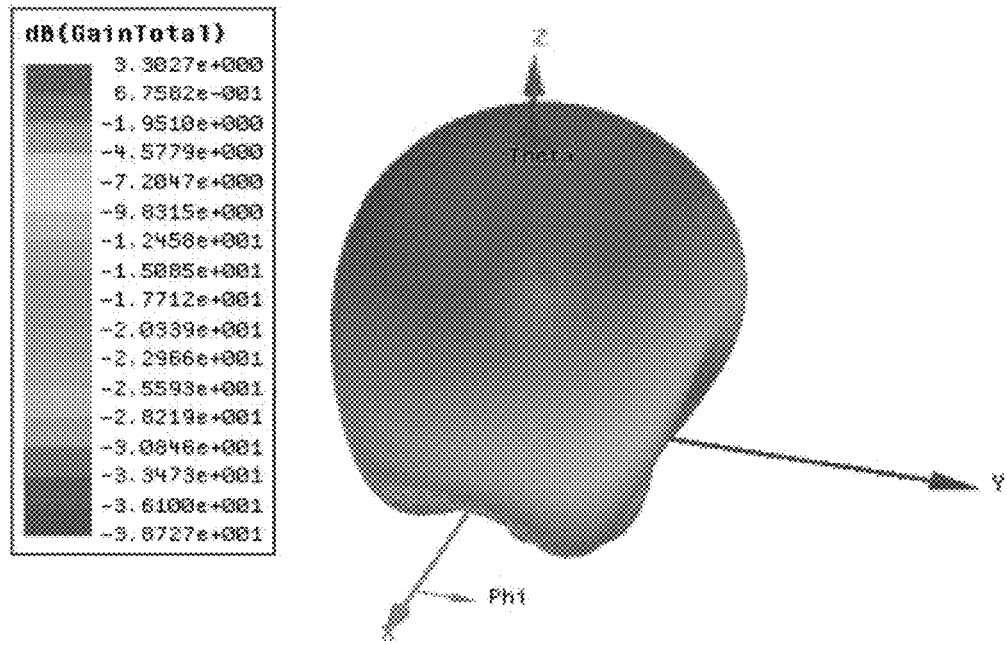
FIG. 7b is a 3-D far field radiation pattern graph for the sensor circuit, in accordance with some embodiments of the present invention.

Based on the measured CNTs 120, 220 surface impedance, discussed below, the CNTs 120, 220 can be modeled as a lumped load comprising a resistance and a capacitance in parallel. The patch antenna 105, 205 can be implemented on paper substrate using this load termination in appropriate software (e.g., HFSS) and the return loss and radiation pattern can be simulated. FIG. 7a depicts how the change in CNTs impedance affects the return loss of the layout shown in FIG. 2. As shown, the increase in resistance shifts the return loss to higher frequencies, whereas the increase in capacitance reduces the return loss (i.e., changes the amplitude without much frequency shift). As shown in FIG. 7b, using only a small portion of the antenna sensor to deposit CNTs enables the design to maintain an acceptable gain of approximately 3.3 dBi.

Material Properties and Characterization

Printing Setup

For improved marketability, it is desirable to produce PABS-SWNT sensors that are both cost-effective and environmentally friendly. Neither of these goals is met with conventional photolithography techniques. One promising solution, however, is inkjet printing of conductive particles on paper sheets. Paper possesses a number of useful attributes, making it suitable for low-cost "green" electronics. Because it is cellulose, for example, it is considered a renewable resource. Additionally, paper can be easily processed into reels, sheets, and other forms that enable a variety of low-cost manufacturing solutions. Ink jet printing is widely known in electronic applications and is almost ubiquitous in both home and office applications.

In addition, recent advances in inkjet printing enable the use of new functional materials, such as conductive and CNT-based inks, leading to an increased deployment in printed electronics, such as, for example and not limitation, flexible displays, RF identification tags (RFIDs), sensors, solar panels, fuel cells, batteries, and antennas. Inkjet printing for RF applications is challenging, however, because precise control of the conductivity and surface integrity of the final product is required.

In general, there are at least two factors that affect the print quality: (1) the ink properties and (2) the settings of the printing system. Some notable ink properties to observe are viscosity, surface tension, and dispersion stability. Printing with an ink of high viscosity and high surface tension at a high contact angle, for example, produces smaller sized dot patterns. The volume of the jetted ink, the traveling velocity of the ejected droplet, the gap distance between each droplet, the printing frequency, the temperature of the jetted ink, the temperature of the substrate, and the sintering/curing mechanism provided by the printing system are among the important factors of the printing system.

Example 2

A DMP-2800 tabletop inkjet printer is available from Dimatix, Inc., Santa Clara, Calif.[6] To ensure good RF properties of the final product, an in-house recipe was developed taking into account all of the aforementioned parameters that affect the print quality. For all RF traces, such as the patch antenna, Dimatix 1-pL silver nanoink cartridges (DMC-11601) are kept at a distance of 0.5 mm from the surface of the paper. The printer head is first adjusted to achieve a print resolution of 2540 dpi, which ensures good RF conductivity (i.e., approximately $9 \times 10^6$ S/m), up to several gigahertz. Conductive ink CCI-300 from Cabot Corporation, Billerica, Mass.,[7] is then jetted through the cartridges at a temperature of 40° C., with the paper substrate maintained at 60° C. Each printed device is then cured in a thermal oven for approximately 2 h at 120° C.

[6] www.dimatix.com

[7] www.cabot-corp.com

Paper Characterization

Embodiments of the present invention can also comprise a measurement-based RF surface impedance model for a thin-film of SWNT printed on paper. It is possible to incorporate this model as a lumped circuit element in a commercial electromagnetic (EM) solver, such as HFSS, to design planar antennas or sensors on paper substrate that involve CNT loading of some kind. The dielectric properties of the benchmarking paper substrates can be studied through the use of a split-post dielectric resonator technique.[8] To ensure accuracy, each blank paper sample can be thermally cured prior to testing to mimic the curing process used during inkjet printing of the final product.

[8] See, J. Kupka, R. N. Clarke, O. C. Rochard, and A. P. Gregory, "Split post dielectric resonator technique for precise measurements of laminar dielectric specimens: measurement uncertainties," *Microw., Radar, Wireless Commun.*, vol. 1, pp. 305-308, 2000; "Split post dielectric resonators for dielectric measurements of substrates," Agilent Technol., Santa Clara, Calif., Agilent Appl. Note, 2006; see also http://cp.literature.agilent.com/litweb/pdf/5989-5384EN.pdf; G. Shaker, S. Safavi-Naeini, N. Sangary, and M. Tentzeris, "Inkjet printing of ultra-wideband (UWB) antennas on paper-based substrates," *IEEE Antennas Wireless Propag. Lett.*, vol. 10, pp. 111-114, 2010.

Example 3

Figure 8A:
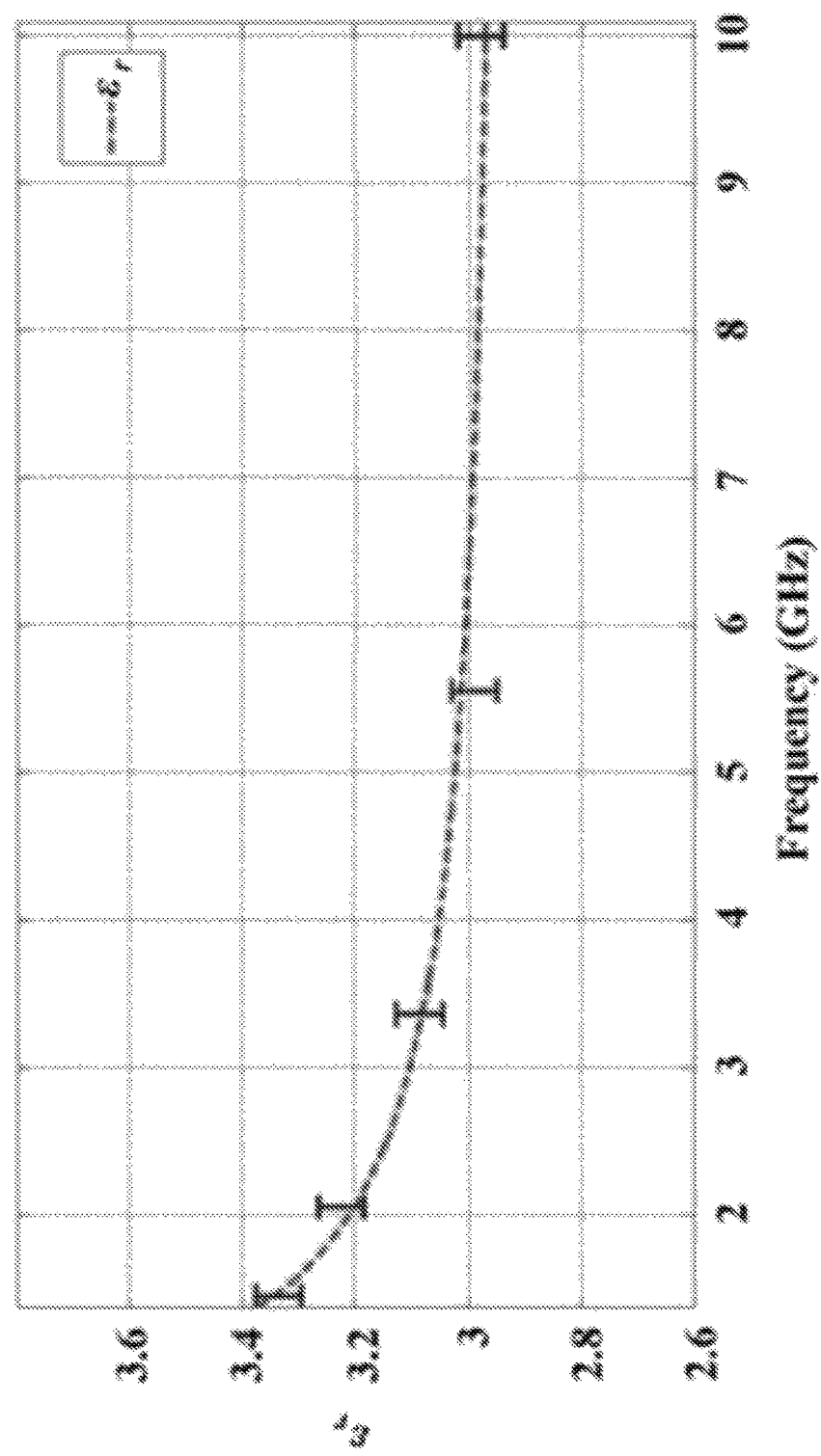
FIG. 8a is a graph depicting the characterization of a paper material using a split-ring resonator method, in accordance with some embodiments of the present invention.

The paper substrate was cured first in a thermal oven for 2 h at 120° C. to mimic the curing process of the printed ink. The results for the extracted relative permittivity of the 10-mil-thick cured paper are shown in FIG. 8a. The measured dielectric loss tangent values were bounded between 0.06-0.07 up to 10 GHz.

Silver Ink Characterization

The conductivity of the printed conductive ink can be measured in an number of ways, including, for example and not limitation, using a Signatone four-point probe.[9] To ensure consistency and good RF conductivity, multiple layers of ink can be printed.

[9] www.signatone.com.

Example 4

Three layers of ink were printed, and then treated in a thermal oven for 2 h at 120° C. The resulting ink thickness was measured using a Wyko Profilometer.[10] The thickness was approximately 3 μm and the dc conductivity consistently measured from approximately $9\times10^6$ S/m to $1.1\times10^7$ S/m.

[10] www.veeco.com.

CNT Characterization

In some embodiments, the CNTs film can be deposited on photographic paper, or other suitable substrate, for the antenna sensor. As a result, the paper (or other substrate) can first be characterized by itself, and then the substrate with CNTs can be characterized, to determine their dielectric properties. This can be done, for example, using a rectangular waveguide set-up. In this configuration, the sample can be sandwiched between two calibrated waveguides, and the transmission (or insertion loss) thereof can be measured on a network analyzer. In some embodiments, the dielectric constant of paper can be calculated using a standard iterative inversion method, or other suitable method, using measured transmission scattering parameter (or transmission coefficient), or S21, data.

Figure 8B:
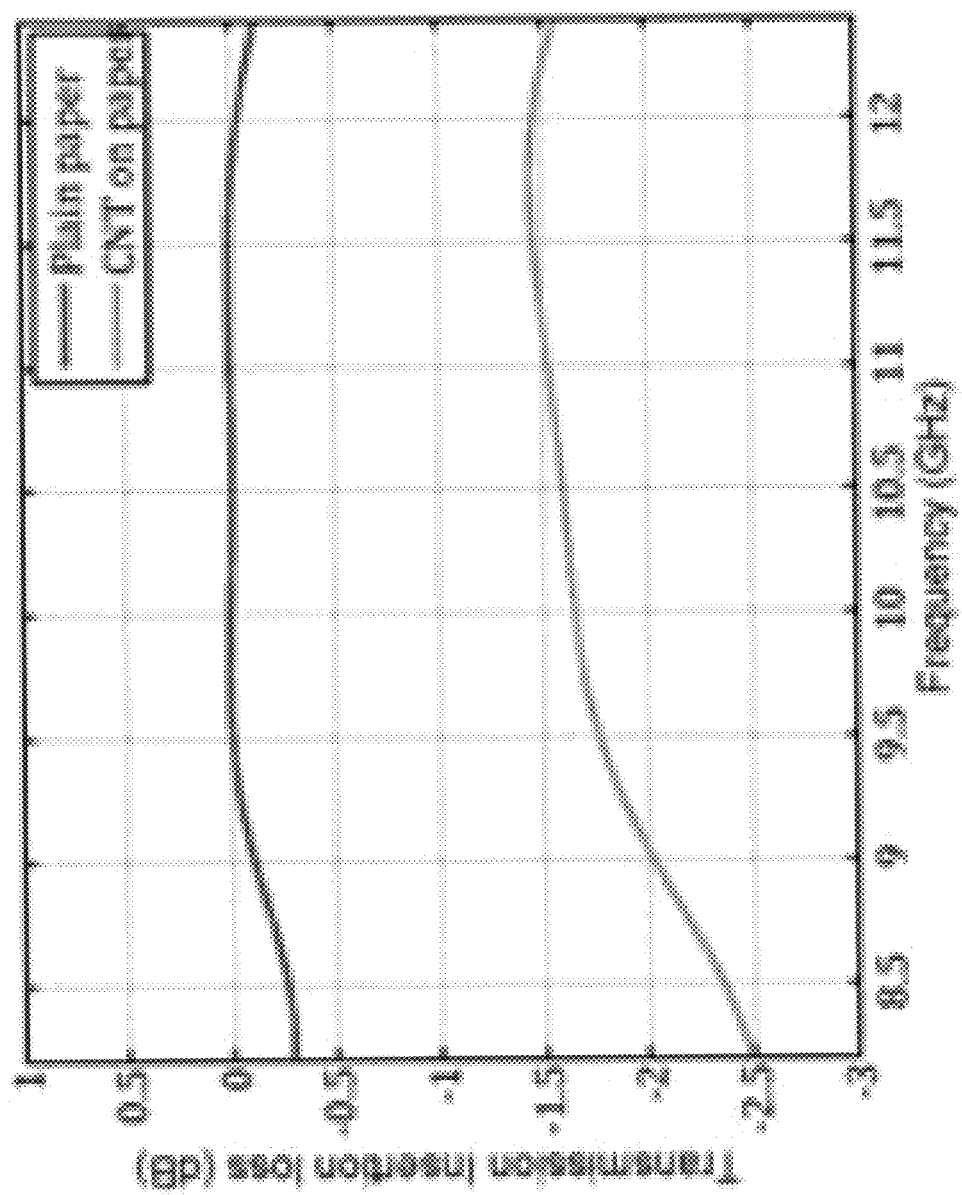
FIG. 8b is a graph depicting the measured insertion loss of the paper material, in accordance with some embodiments of the present invention.

As shown in FIG. 8b, the insertion loss for paper is less than approximately 0.2 dB in the X-band. On the other hand, the second measurement on paper with CNTs lowers the transmission coefficient by ~2 dB due to conductive losses in the CNTs. Since the latter is a composite of the two materials, permittivity of the CNTs cannot be determined directly from the measured data. However, using the data in FIG. 8b, the complex dielectric constant of paper can be calculated to be around 3.5+j0.02 in the X-band (i.e., 8.5 to 12 GHz). Using the measured permittivity of paper and the measured S21 of the paper plus CNTs combination, the surface impedance of the CNT film (approximately 10 microns thick) can be calculated using the relation:

$$Z_s = S_{21}Z_0 \frac{\Gamma^2\tau^2 - 1 + \Gamma(\tau^2 - 1)}{2(\Gamma^2 - 1) - 2S_{21}(\Gamma^2\tau^2 - 1)}$$

where $Z_0$ is the characteristic impedance of the waveguide mode, while $\Gamma$ and $\tau$ are the reflection coefficient at the air/substrate interface and the transmission phase, respectively, for a specified paper thickness, t. These are given by:

$$\Gamma = \frac{\sqrt{\frac{\mu}{\varepsilon}} - 1}{\sqrt{\frac{\mu}{\varepsilon}} + 1} \quad \text{and} \quad \tau = e^{-tk_0 t\sqrt{\mu\varepsilon}}$$

where $\in$ and $\mu$ are relative permittivity and permeability, respectively, of the paper substrate. The relative permeability, $\mu$, is approximately 1 for paper. The wavenumber in free space is "dented" by $k_0$.

Figure 9:
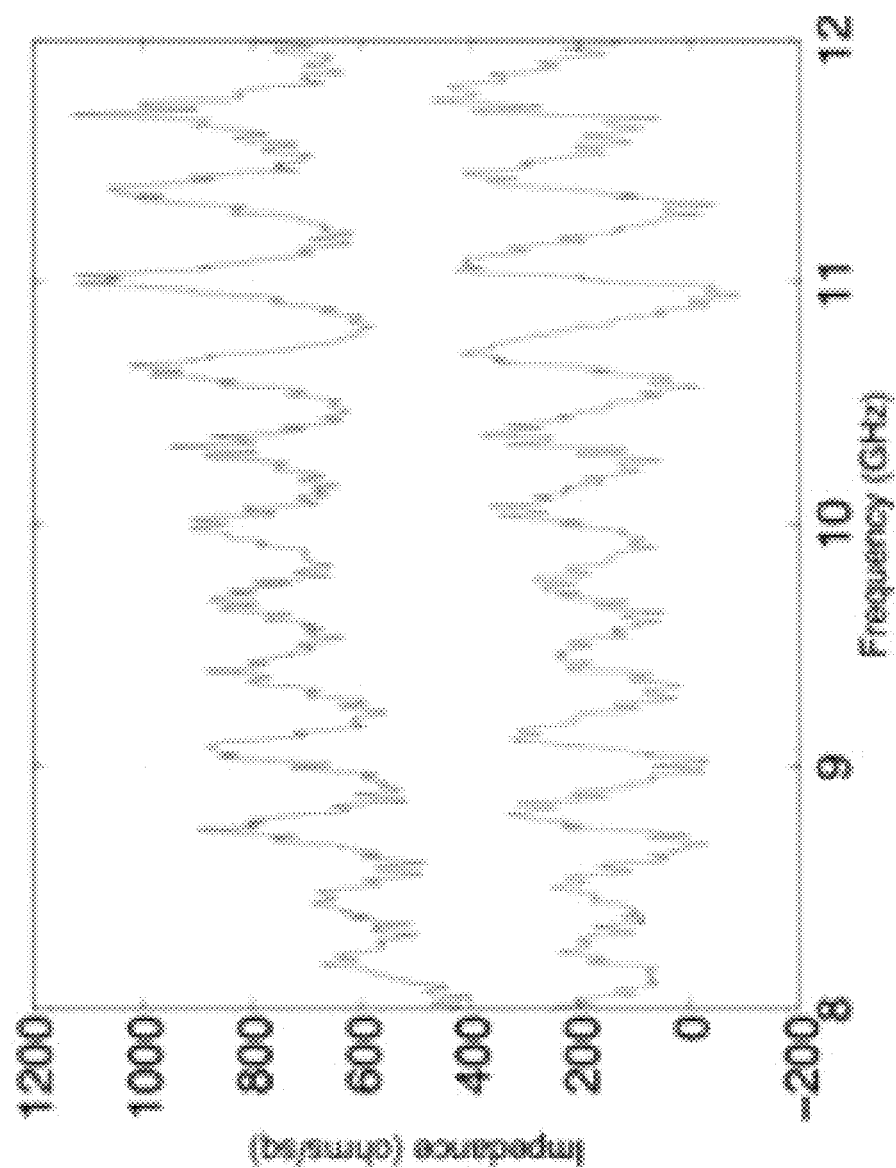
FIG. 9 is a graph depicting the surface impedance of the CNT film, with the top curve denoting the real part and the bottom denoting the imaginary part, in accordance with some embodiments of the present invention.

The calculated surface impedance of the CNT film can be depicted as in FIG. 9. The fluctuations can be attributed to the air-gap between the specimen and the waveguide, which can cause errors, particularly with thin conductive specimens. These errors can be reduced by performing transmission line measurements directly on the CNT/paper sample and employing thru-reflect-line (TRL) calibration standards that are specifically constructed for the CNT conductor geometry. The paper substrate is nonetheless sufficiently characterized by a dielectric constant of 3.5 and the CNTs by a surface impedance of (+j 100) ohms per square, at 6 GHz (i.e., the design frequency of the sensor). The CNTs impedance can be obtained from FIG. 9 by smoothing the data using a linear fit, or other suitable regression, and extrapolating the result down to 6 GHz.

Figure 10:
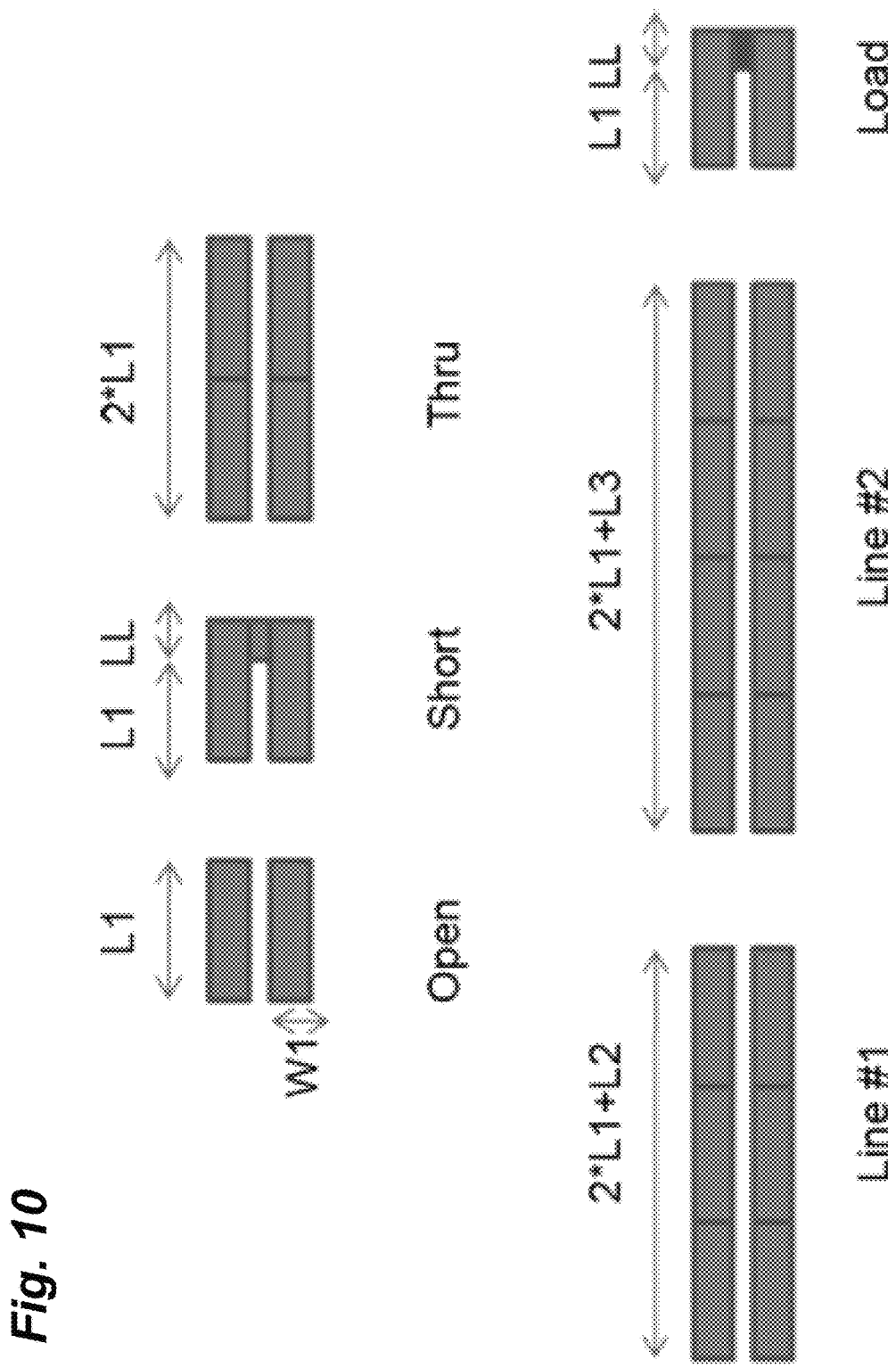
FIG. 10 is a schematic depicting thru-reflect-line (TRL) calibration, in accordance with some embodiments of the present invention.

For improved characterization, the RF characterization of the deposited CNT layers can be performed using a two-tier calibration process. First, a short-open-load-thru (SOLT) calibration process can be applied up to the coaxial feed of the SMA connector. Next, a custom-designed multiline TRL calibration set using silver coplanar strip lines can be used to calibrate to the reference plane at the edge of the CNT pad. FIG. 10 depicts a schematic of such a custom set, where W1 denotes the strip width, L1 denotes the length up to the calibration reference plane, and LL denotes the physical lengths of the line short and of the load termination. L2 and L3 are different line lengths used in the calibration procedure. The TRL calibration can be utilized to extract the bulk RF behavior of the CNT thin-film.[11]

[11] R. B. Marks, "A multiline method of network analyzer calibration," *IEEE Trans. Microw. Theory Tech.*, vol. 39, no. 7, pp. 1205-1215, July 1991.

Figure 11:
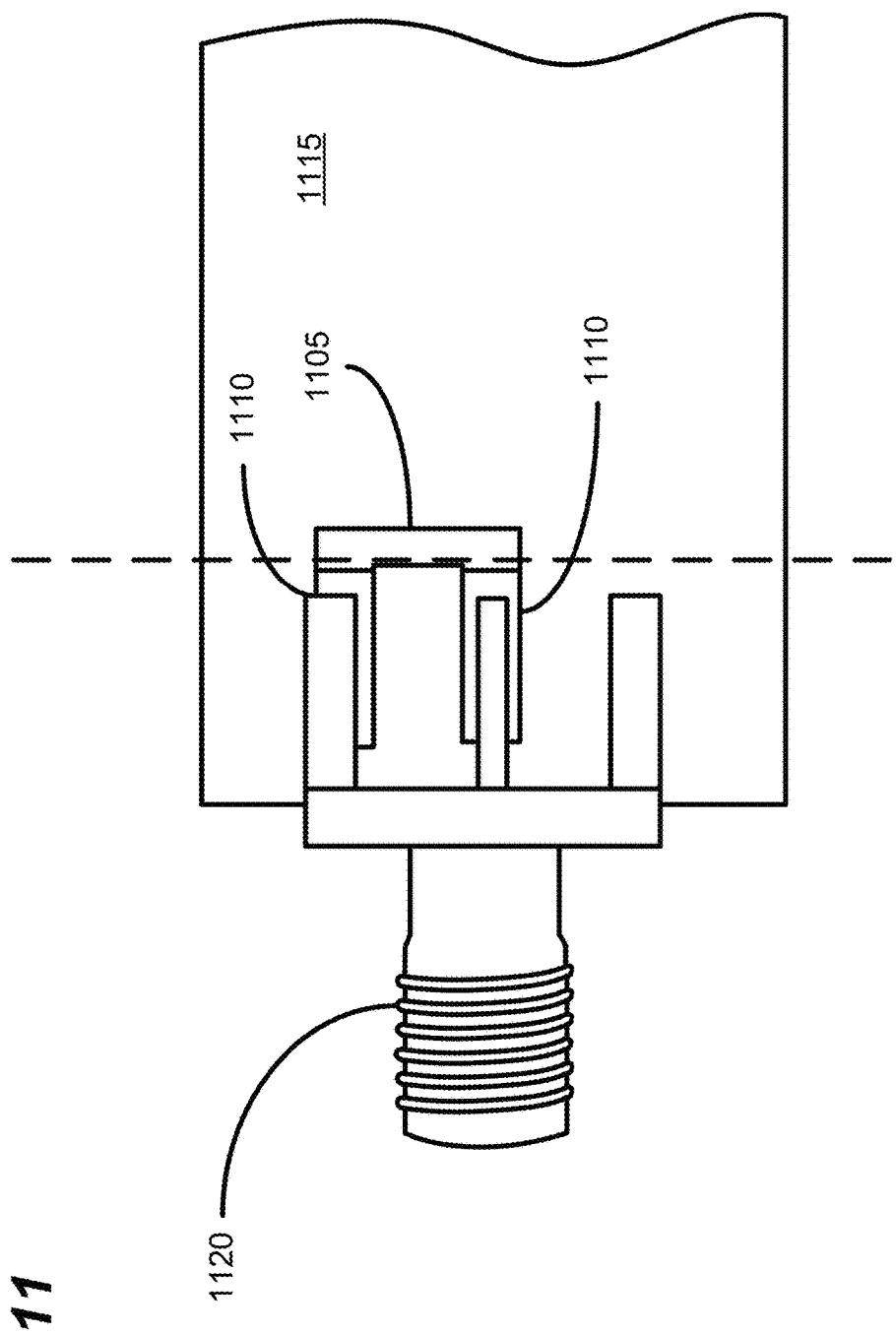
FIG. 11 is a schematic of CNT film placed at the edge of printed silver lines, in accordance with some embodiments of the present invention.

In some embodiments, the silver lines can be printed such that they form a set of coupled lines. The CNT layer can be deposited as a thin-film at the TRL reference plane. Using the TRL calibration set, therefore, it is possible to remove from the calculation the influence of feed transmission lines up to the reference plane and extract the input admittance at that plane. A sample of the CNT film 1105 deposited between two electrodes 1110 on the paper substrate 1115 is shown in FIG. 11. In some embodiments, the fabrication process can comprise printing silver nanoink to form the electrodes 1110 on photo paper 1115, followed by the application of an SWNT thin-film layer 1105 proximate the electrode 1110 edges. The dashed line in FIG. 11 approximately represents the reference plane used in the TRL extraction algorithm.

The extraction for various samples with different thicknesses of the SWNT film 1105 revealed that the RF behavior of CNT layers 1105 can be adequately modeled through a parallel RC tank circuit. Such R and C values are primarily functions of the frequency, the geometrical configuration, and the concentration and material properties of the deposited CNT film 1105.

Figure 12:
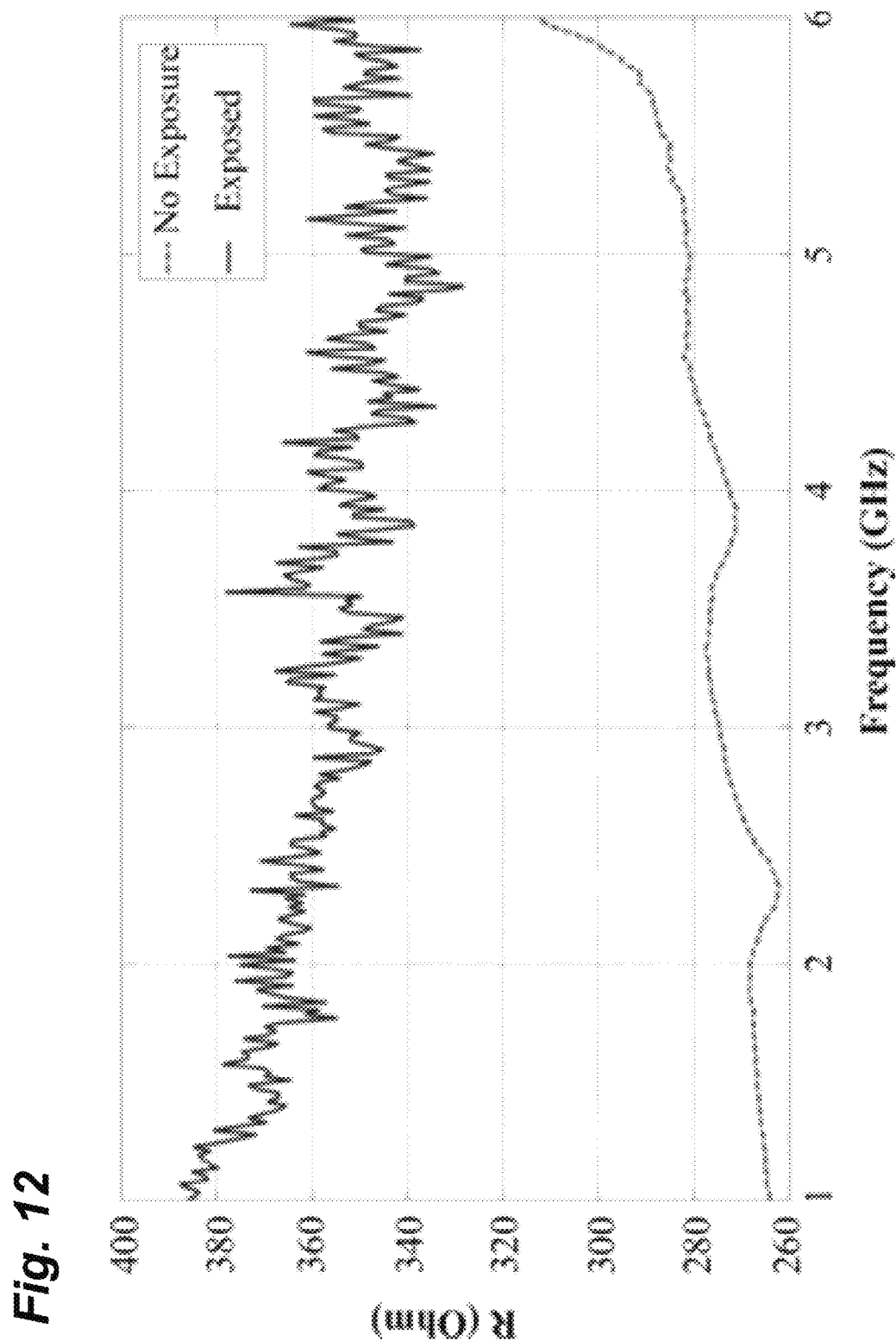
FIGS. 12 and 13 are graphs depicting equivalent resistance of the CNT film before and after exposure to ammonia, in accordance with some embodiments of the present invention.
Figure 13:
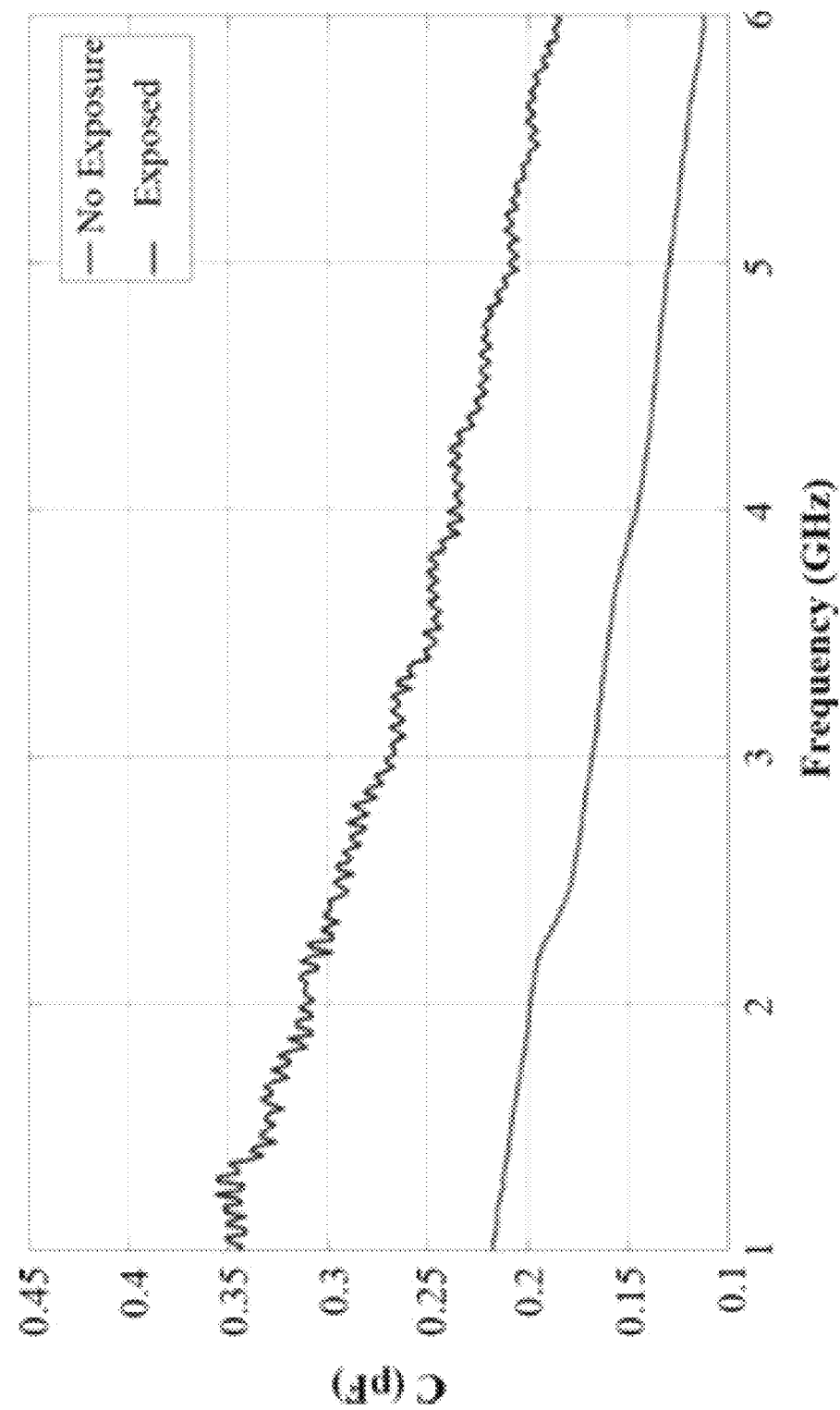

FIGS. 12 and 13 depict sample results for the extracted resistance and capacitance of a CNT film 1105 of dimensions 1 mm×4 mm deposited at the gap between the electrodes 1110, shown in FIG. 11. The total thickness of the CNT film 105 using ten layers is 11 μm. As shown in FIGS. 12 and 13, at higher frequencies, the losses in the SWNT film increase, while the capacitance decreases. It should be noted, however, that the resulting equivalent resistance and capacitance can be controlled to a desired value by altering the dimensions of CNT thin-film (e.g., the width and length) and the volume density of SWNTs (or equivalently, the film thickness).

Example 5

Figure 14:
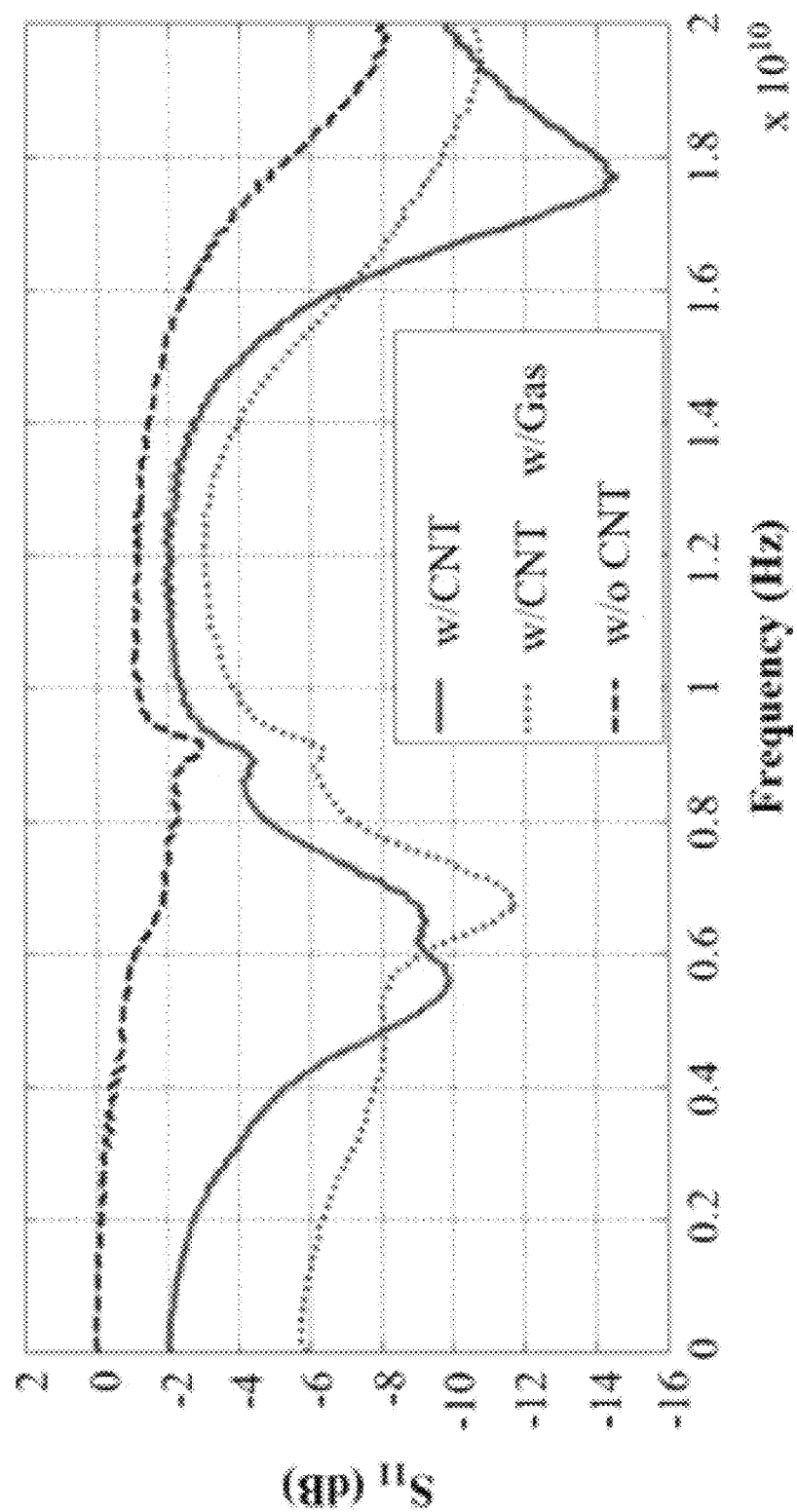
FIG. 14 is a graph depicting the input reflection coefficient at the connector coaxial feed, in accordance with some embodiments of the present invention.

The test fixture shown in FIG. 11 was subjected to ammonia of concentration 50 ppm in a closed cell system. FIG. 14 shows the input reflection coefficient at the coaxial feed 1120 of the SMA connector for three distinct cases. The first is without a CNT connector 1105 (i.e., an open-ended transmission line). The second is with CNT 1105, but before gas exposure. The third is with CNT 1105 after gas exposure. It is evident from FIGS. 12 and 13 that the CNT film 1105 shows a clear change in its RF properties (see the discussion below) upon gas exposure. This, in turn, results in a noticeable frequency shift in the input reflection coefficient. FIG. 13 is indicative of the overall behavior of the printed silver ink 1110 and the CNT thin-film 1105 on the paper substrate 1115.

The equivalent admittance of the exposed CNT thin-film 1105 can be extracted using the TRL scheme outlined above. The extracted resistance and capacitance values can then be compared with those for the case without ammonia exposure, as plotted in FIGS. 12 and 13, respectively. As shown, both the resistance and capacitance of the exposed film increase due to the adsorption of ammonia molecules on the PABS-SWNT thin-film. The losses in the CNT film 1105 due to ammonia exposure are higher, but are not significantly dependent on frequency. The trend in capacitance variation with frequency, on the other hand, is similar with and without ammonia exposure.

V. Controlled Sensor Measurement

Test 1

Figure 15:
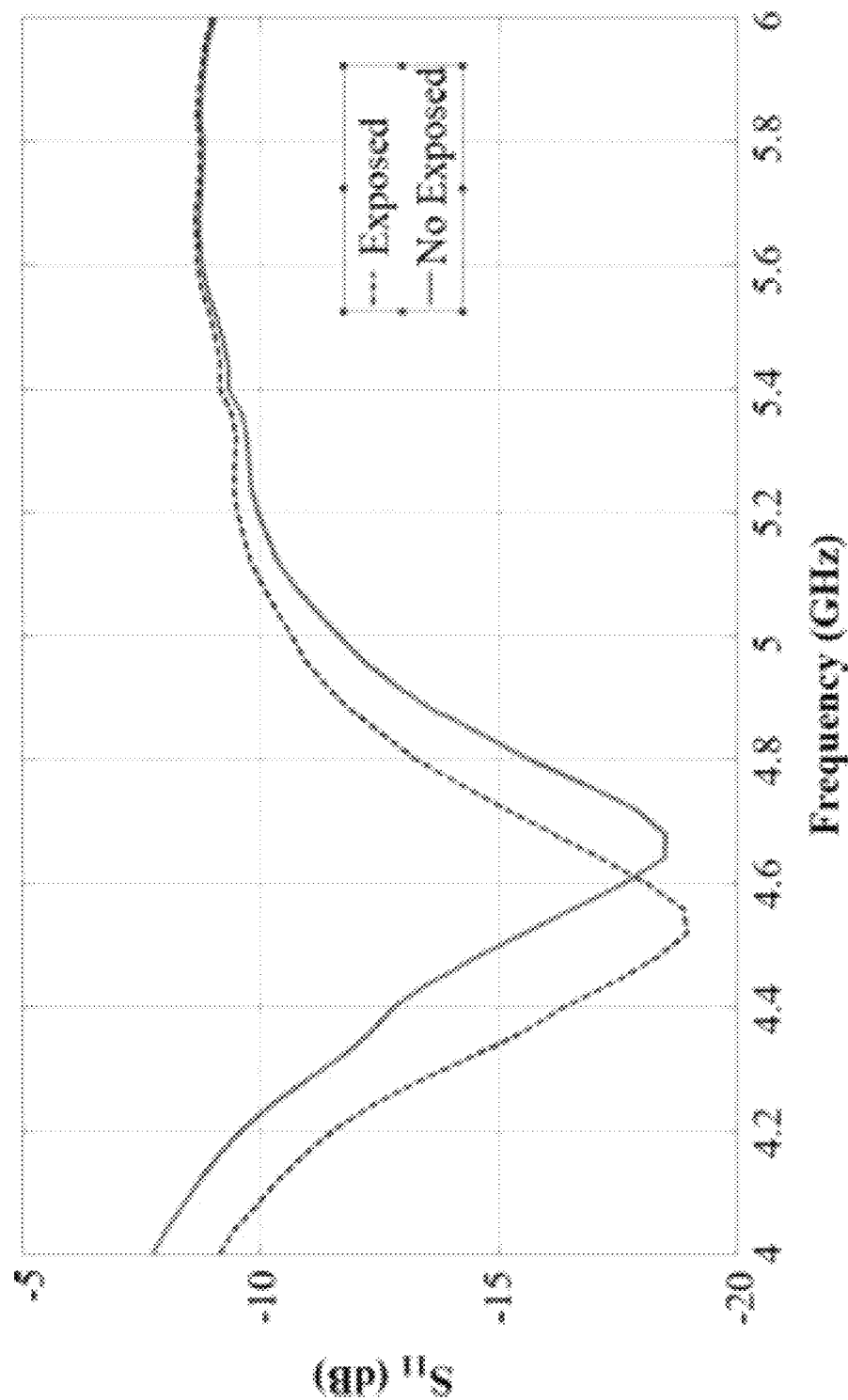
FIG. 15 is a graph depicting the frequency shift of the sensor after exposure to household ammonia, in accordance with some embodiments of the present invention.

To evaluate the sensor performance for the sensor design shown in FIG. 1, house-hold ammonia—approximately 10% ammonium hydroxide—in a small plastic container can be used, with the antenna placed nearby. The input reflection coefficient can then be recorded before and after filling the container with ammonia. The resulting response for these two cases is shown in FIG. 15. As shown, a resonance frequency shift of approximately 120 MHz is observed. Notably, this response is approximately 25 times greater than that provided by conventional CNT gas sensors and the response time was less than 30 seconds.

This empirical measurement also agrees qualitatively with the equivalent circuit model for the CNT film represented in FIGS. 12 and 13, which predicts a resonance shift to lower frequencies caused by increase in resistance/capacitance due to $NH_3$ interaction with CNT. Such measurements confirm the principle of operation of the sensor. To confirm the sensitivity, however, it may be desirable to determine the minimum gas concentration needed to trigger a noticeable shift in the resonant frequency. To this end, a more controlled measurement system can be deployed.

Test 2

To provide a more controlled measurement several components can be including such as, for example, a gas generator, an $NH_3$ permeation tube, a closed-system sensor cell, an Agilent PNA-L N5230A programmable network analyzer (PNA), and a data acquisition system. In this case, a 491M gas generator and an $NH_3$ permeation tube from the Kin-Tek Company were used.[12] At all times, this system was used under a chemical fume hood.

[12] "491M", Kin-Tech Corporation, La Marque, Tex., available at http://www.kin-tek.com/.

The $NH_3$ permeation tube has a calibrated emission rate under controlled temperature. Dry nitrogen was delivered from an ultra high purity (Grade 5) compressed nitrogen gas cylinder from Airgas. By controlling the ammonia emission rate and the nitrogen flow rate, desired concentrations (in the ppm range) of ammonia were generated from the gas generator. Before each ammonia exposure test, the $NH_3$ permeation tube was installed in the gas generator and heated to a predetermined temperature for around 4 h in order to obtain a stabilized ammonia concentration. The accuracy of gas concentration output is ±4% according to the calibration results from Kin-Tek. The sensor can then be installed inside a closed test cell and a concentrated $NH_3$ stream can be delivered into the test cell via a Teflon tube. The CNT film portion of the sensor can be placed near the gas inlet port, such that the ammonia stream interacts with the sensor surface first.

For the RF measurement, expendable connectors and a precision phase-steady cable assembly can be used to interface between the PNA and the antenna. A short-open-load (SOL) one-port calibration was conducted using coaxial standards. Measurements were made at three different concentrations: 50, 75, and 100 ppm. For each measurement, the data was saved automatically every 10 s. Each measurement consisted of several minutes of baseline recording during which the sensor was exposed to pure nitrogen, purging the container. This was followed by exposure to ammonia, after which the system was again purged with nitrogen gas to bring the sensor back to the baseline.

Based on the measured data for the three concentrations, and as expected, the resonant frequency shift increases with ammonia concentration until the sensor saturates. The resonant frequency shift is summarized in Table I along with the nitrogen flow rate required to maintain appropriate ammonia concentration from the 491M Gas Generator during the exposure and reversion phases (i.e., back to ambient conditions).

TABLE 1

MEASUREMENT RESULTS

| Conc. Ammonia (ppm) | Exposure Flow Rate (L/min) | Reversion Flow Rate (L/min) | Δfres of S11 (MHz) |
|---|---|---|---|
| 50 | 0.46 | 0.5 | 43.125 |
| 75 | 0.31 | 5.0 | 46.875 |
| 100 | 0.23 | 0.5 | 48.750 |

Figure 16:
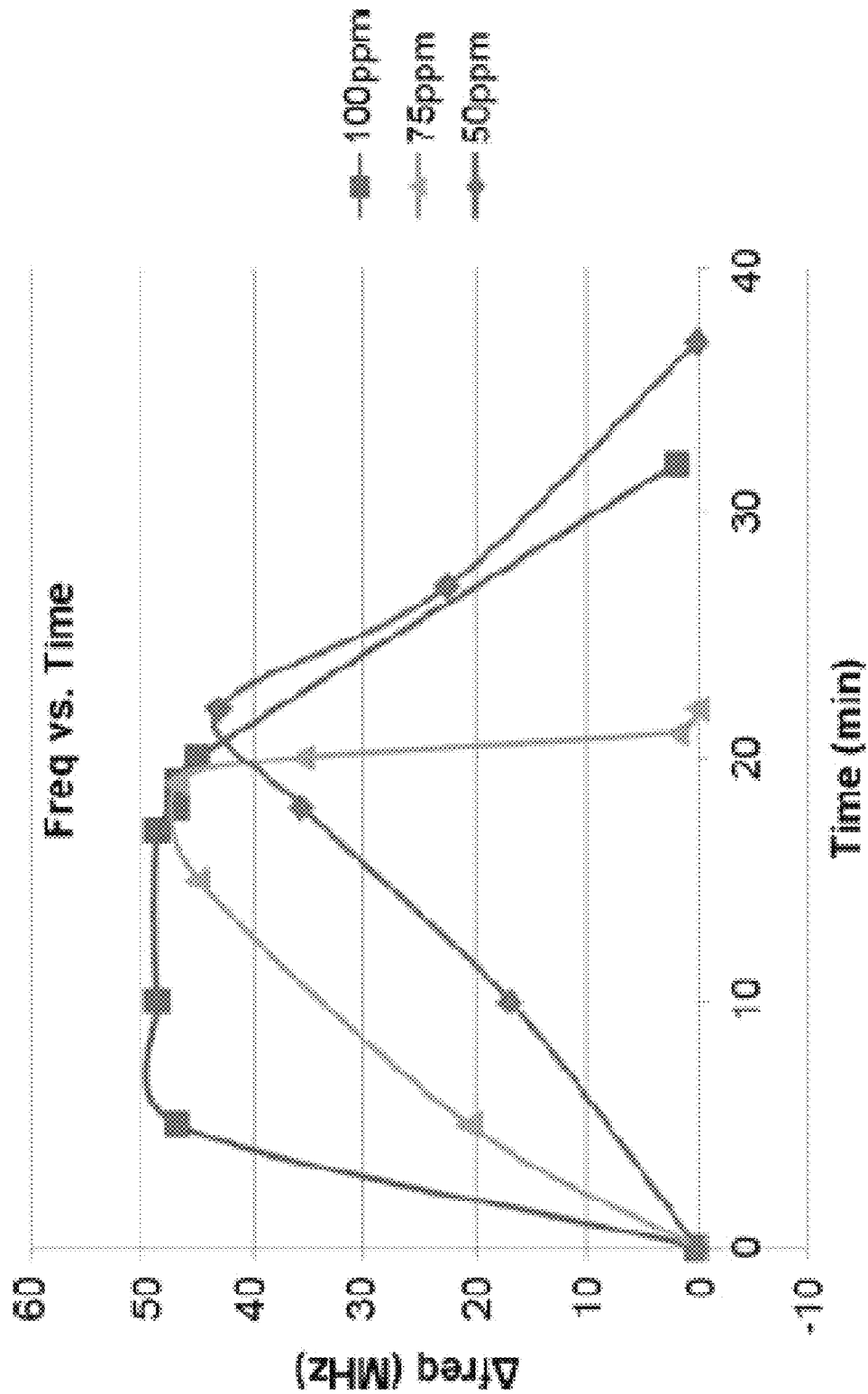
FIG. 16 is a graph depicting the frequency shift with respect to time for three different concentrations of ammonia, in accordance with some embodiments of the present invention.

As shown in FIG. 16, gas concentration affects at least two things: (1) the time it takes to reach saturation and (2) the saturation level itself (or the maximum frequency shift). The 100 ppm concentration, for example, shows the steepest slope to saturation and the highest shift at 48.75 MHz, while the 50 ppm concentration shows the slowest response and the lowest shift at 43.125 MHz.

After exposing the sensor to ammonia for approximately 18 min, the closed system was purged of ammonia using nitrogen gas. In the third column of Table I, reversion flow rate indicates the flow rate of nitrogen gas used to flush out the closed cell system to return the input reflection coefficient of the antenna to its baseline. Two different flow rates, 0.5 and 5 L/min, were used to observe the difference in reversion. As also shown in FIG. 16, it is clear that higher nitrogen gas flow during reversion causes the sensor to return to baseline faster.

Figure 17:
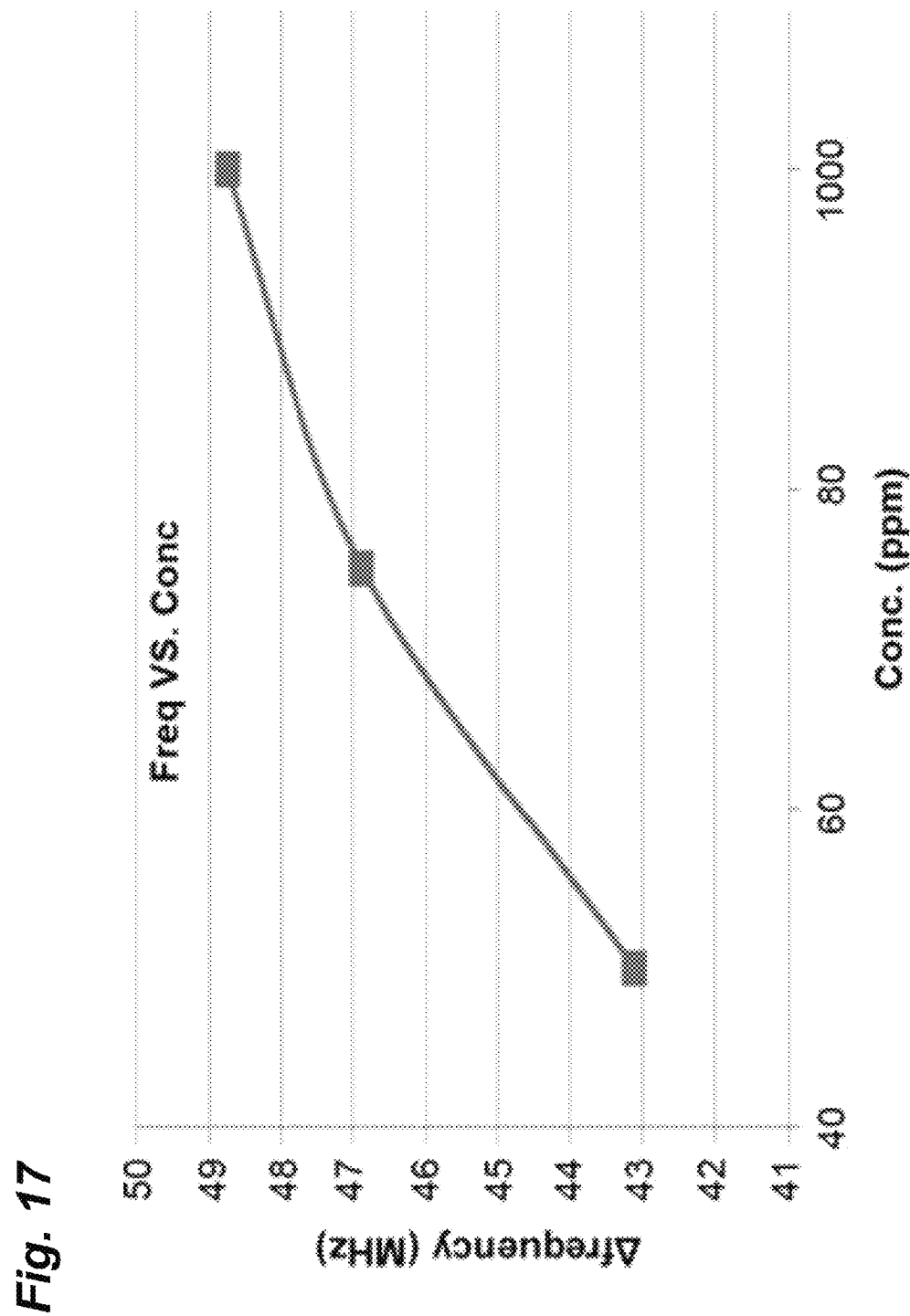
FIG. 17 is a graph depicting the frequency shift with respect to concentration for ammonia, in accordance with some embodiments of the present invention.

FIG. 17 plots the maximum shift in frequency against ammonia concentration. As expected, the higher concentration yields a larger resonant frequency shift. FIG. 17 also shows a decreasing amount of shift for incrementally higher concentrations in excess of approximately 80 ppm level. This tends to indicate a trend towards saturation of the sensor with ammonia. Of course, because the sensor is capable of detecting very low concentrations, e.g., for the detection of poisonous gases, this is of little consequence.

Test 3

A similar test was performed to determine the efficacy of the sensor design shown in FIG. 2. As before, return loss measurements of the antenna sensor were conducted using an ammonia gas permeation tube, a vacuum hood, and a programmable network analyzer. The concentration of ammonia was controlled electronically using the permeation tube and an auxiliary source of nitrogen. The antenna was clamped under the hood, and ammonia, mixed with appropriate quantity of nitrogen, was released over the surface of the sensor. Return loss of the antenna was measured in ambient air under the hood for 3 minutes first to establish baseline. Next, 25 ppm ammonia was released over the sensor for 3 minutes and the return loss was measured at periodic intervals. Finally, the ammonia was mixed with nitrogen to bring the environment back to ambient, and the sensor was examined for 10 min. to ensure it would revert back to its nominal condition before exposure.

Figure 18:
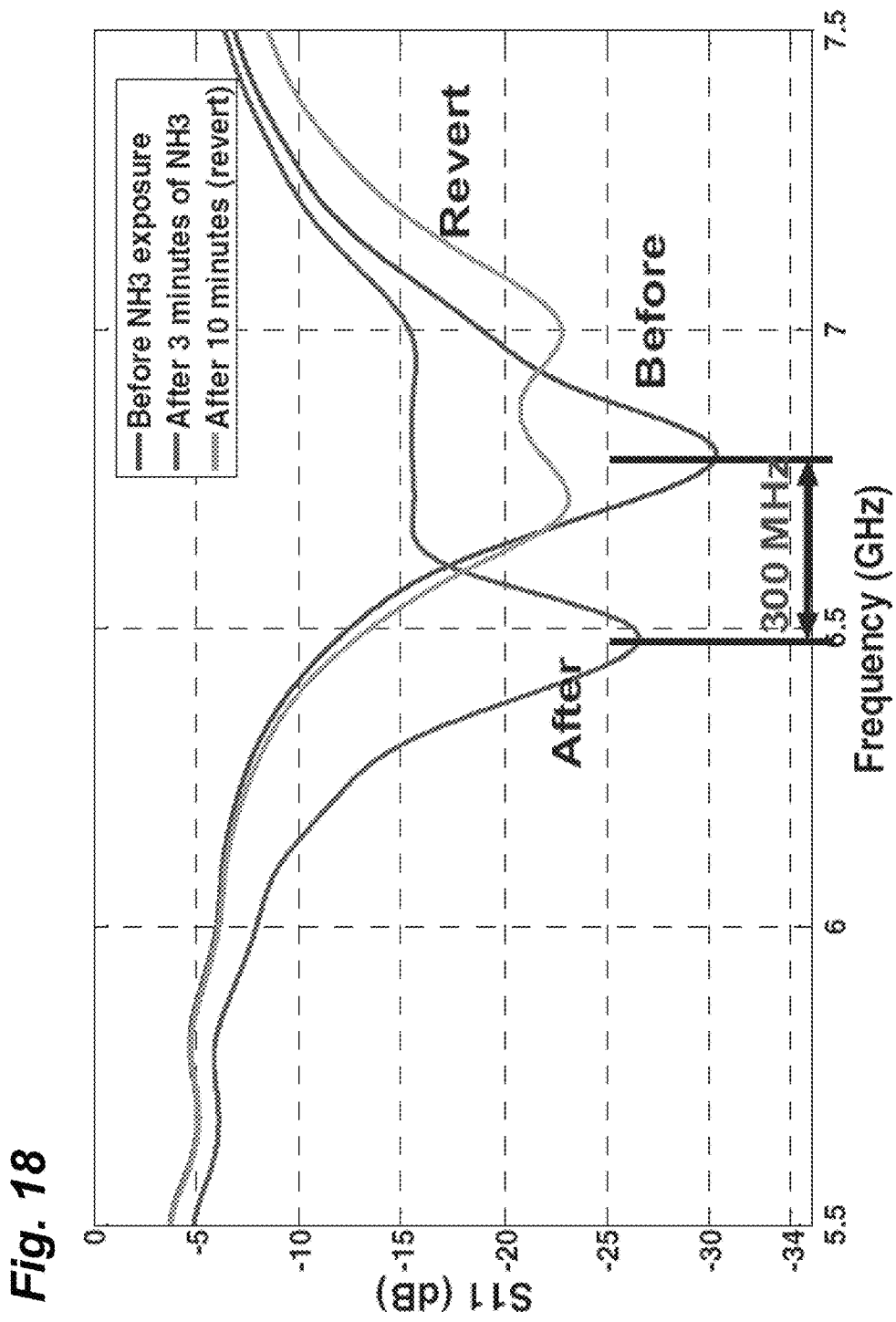
FIG. 18 is a graph depicting measured return loss with ammonia gas showing a resonance frequency shift of 300 MHz when exposed to 25 ppm ammonia, in accordance with some embodiments of the present invention.

FIG. 18 shows the return loss for the three states and clearly demonstrates a shift of 300 MHz in resonance when exposed to 25 ppm ammonia. After purging the environment of ammonia, the sensor substantially reverted to the original resonance at approximately 6.8 GHz.

Summary

Embodiments of the present invention relate to a modified patch antenna topology for use as an ammonia gas sensor using functionalized PABS-SWNT as the sensing agent and inkjet-printing implementation. The sensor has demonstrated a maximum sensitivity of 300 MHz resonance frequency shift at an operating frequency of approximately 6.8 GHz. This shift is the highest reported by orders of magnitude with respect to conventional CNT-based sensors. This inkjet-printed gas sensor can be easily integrated with RFID chips, and other components to provide low-cost "smart skin" applications, for example, in remote wireless chemical and biological sensing.

As discussed above, embodiments of the present invention relate to a highly sensitive antenna-based CNT sensor, which provides gas detection by detecting a resulting shift in resonant frequency of the sensor circuit upon gas exposure. In some embodiments, RF characterization can be performed experimentally on a patch of thin-film PABS-SWNT located between two printed electrodes and a surface impedance model for the SWNT film can be derived. The resulting impedance model for the SWNT film can be shown to be equivalent to a parallel RC circuit in which both the R and C values change with exposure to ammonia. Utilizing the derived impedance model, a sensor can be designed using a loaded patch antenna topology, with the loading provided by appropriately positioned SWNT film.

Experimental measurements show a frequency shift of 43-49 MHz for ammonia concentrations ranging from 50 to 100 ppm for the sensor design shown in FIG. 1 and a frequency shift of up to 300 MHz for the sensor design in FIG. 2. This change in the resonant frequency qualitatively validated the characterization model and the sensors demonstrate both high sensitivity at low concentrations and a fast return to baseline. Embodiments of the present invention can be used for remote sensing and can be integrated with RFID or wireless identification and sensing platform (WISP) tags for low-cost wireless gas sensing applications.

While several possible embodiments are disclosed above, embodiments of the present invention are not so limited. For instance, while several possible configurations of materials for the sensor have been disclosed, other suitable materials and combinations of materials could be selected without departing from the spirit of embodiments of the invention. In addition, the location and configuration used for various features of embodiments of the present invention can be varied according to a particular application that requires a slight variation due to, for example, space or power constraints. Such changes are intended to be embraced within the scope of the invention.

The specific configurations, choice of materials, and the size and shape of various elements can be varied according to particular design specifications or constraints requiring a device, system, or method constructed according to the principles of the invention. Such changes are intended to be embraced within the scope of the invention. The presently disclosed embodiments, therefore, are considered in all respects to be illustrative and not restrictive. The scope of the invention is indicated by the appended claims, rather than the foregoing description, and all changes that come within the meaning and range of equivalents thereof are intended to be embraced therein.

What is claimed is:

1. A gas sensor for sensing an analyte comprising:
    a patch antenna with a first end;
    a feed line with a first end and a second end opposite the first end, the second end in mechanical and electrical communication with the first end of the patch antenna;
    a carbon nanotube (CNT) thin-film layer isolated from the patch antenna and deposited in a gap of a stub line, the CNT thin-film layer having a first end and a second end opposite the first end, the first end in mechanical and electrical communication with the feed line; and
    the stub line isolated from the feed line and having a first end and a second end opposite the first end, the first end in mechanical and electrical communication with the second end of the CNT thin-film layer;
    wherein the gas sensor, including the patch antenna, the feed line, the stub line, and the CNT thin-film layer, are disposed on a single substrate;
    wherein the sensor has an operating frequency outside the presence of the analyte;
    wherein a size of the CNT thin-film layer in the gap results in minimal losses and a relatively high Q of the sensor; and wherein upon interaction of the analyte with the CNT thin-film layer, a capacitance of the CNT thin-film layer increases and the sensor has a sensitivity of greater than 7 MHz resonance frequency shift at the operating frequency.

2. The gas sensor of claim 1, wherein the sensor has an operating frequency of between 4.5-6.8 GHz.

3. The gas sensor of claim 1, wherein the single substrate comprises paper, and wherein the substrate is attached to a ground plane.

4. The gas sensor of claim 1, wherein the CNT thin-film layer comprises single walled carbon nanotubes (SWNTs).

5. The gas sensor of claim 4, wherein the SWNTs are functionalized with a first chemical compound to provide a chemical interaction with the analyte, and wherein the sensor has a sensitivity of greater than 43 MHz resonance frequency shift at an operating frequency.

6. The gas sensor of claim 5, wherein the SWNTs are functionalized with poly(m-aminobenzene sulfonic acid) (PABS).

7. A gas sensor for sensing an analyte comprising:
a patch antenna with a first end and a second end;
a feed line with a first end and a second end opposite the first end, the second end in mechanical and electrical communication with the first end of the patch antenna;
a carbon nanotube (CNT) thin-film layer isolated from the patch antenna and deposited in a gap of a stub line, the CNT thin-film layer having a first end and a second end opposite the first end, the first end in mechanical and electrical communication with the second end of the patch antenna; and
the stub line isolated from the feed line and having a first end and a second end opposite the first end, the first end in mechanical and electrical communication with the second end of the CNT thin-film layer;
wherein the gas sensor, including the patch antenna, the feed line, the stub line, and the CNT thin-film layer, are disposed on a single substrate;
wherein the sensor has an operating frequency outside the presence of the analyte;
wherein a size of the CNT thin-film layer being in the gap results in minimal losses and a relatively high Q of the sensor; and
wherein upon interaction of the analyte with the CNT thin-film layer, a capacitance of the CNT thin-film layer increases and the sensor has a sensitivity of greater than 43 MHz resonance frequency shift at the operating frequency.

8. The gas sensor of claim 7, wherein the sensor has an operating frequency of greater than 4.5 GHz; and
wherein the sensor has a sensitivity of between 43-300 MHz resonance frequency shift at the operating frequency; and wherein the antenna, feed line, and stub line are integrated with the CNT film layer on the first substrate.

9. The gas sensor of claim 8, wherein the substrate comprises a liquid crystal polymer, and wherein the substrate is attached to a ground plane.

10. The gas sensor of claim 7, wherein the CNT thin-film layer comprises single walled carbon nanotubes (SWNTs).

11. The gas sensor of claim 10, wherein the SWNTs are functionalized with a first chemical compound to provide a chemical interaction with the analyte.

12. The gas sensor of claim 11, wherein the SWNTs are functionalized with poly(m-aminobenzene sulfonic acid) (PABS).

13. The gas sensor of claim 1, wherein the patch antenna, the feed line, and the stub line are fabricated using deposition of highly conductive nanoparticles; and wherein the CNT thin-film layer deposited in the gap comprises a mesh of randomly oriented CNTs.

14. The gas sensor of claim 13, wherein the highly conductive nanoparticles include silver nanoparticles.

15. The gas sensor of claim 7, wherein the stub line is in electrical communication with a radiating edge of the patch antenna opposite the feed line thereby controlling a resonant frequency of the gas sensor.

16. The gas sensor of claim 7, wherein the patch antenna, the feed line, and the stub line are fabricated using deposition of highly conductive nanoparticles.

17. The gas sensor of claim 16, wherein the highly conductive nanoparticles include silver nanoparticles.

18. The gas sensor of claim 7, wherein the CNT thin-film layer is defined by a mesh of randomly oriented CNTs deposited in the gap.

* * * * *